United States Patent
Juto et al.

(10) Patent No.: US 9,782,320 B2
(45) Date of Patent: Oct. 10, 2017

(54) DOUBLE STIMULATION

(71) Applicant: CHORDATE MEDICAL AB, Kista (SE)

(72) Inventors: Jan-Erik Juto, Stockholm (SE); Fredrik Juto, Stockholm (SE); Victor Kronestedt, Stockholm (SE); William Holm, Stockholm (SE)

(73) Assignee: CHORDATE MEDICAL AB, Kista (SE)

( * ) Notice: Subject to any disclaimer, the term of this patent is extended or adjusted under 35 U.S.C. 154(b) by 655 days.

(21) Appl. No.: 13/714,634

(22) Filed: Dec. 14, 2012

(65) Prior Publication Data

US 2013/0158449 A1 Jun. 20, 2013

Related U.S. Application Data

(60) Provisional application No. 61/576,782, filed on Dec. 16, 2011.

(30) Foreign Application Priority Data

Dec. 16, 2011 (EP) ..................................... 11194068

(51) Int. Cl.
*A61H 23/04* (2006.01)
*A61H 21/00* (2006.01)
(Continued)

(52) U.S. Cl.
CPC .............. *A61H 1/00* (2013.01); *A61H 9/0078* (2013.01); *A61H 21/00* (2013.01); *A61H 23/02* (2013.01);
(Continued)

(58) Field of Classification Search
CPC ...... A61H 9/0078; A61H 23/04; A61H 21/00; A61H 2230/505; A61H 2230/045;
(Continued)

(56) References Cited

U.S. PATENT DOCUMENTS 901,376 A 10/1908 Roberts
912,205 A 2/1909 Talcott
(Continued)

FOREIGN PATENT DOCUMENTS

CH 329193 A 4/1958
EP 0935980 A1 8/1999
(Continued)

OTHER PUBLICATIONS

Papon et al., "Nasal wall compliance in vasomotor rhinitis," J. Appl. Physiol., vol. 100, 2006 (First published Sep. 1, 2005), pp. 107-111, XP055055268.
(Continued)

*Primary Examiner* — Justine Yu
*Assistant Examiner* — Douglas Sul
(74) *Attorney, Agent, or Firm* — Birch, Stewart, Kolasch & Birch, LLP

(57) ABSTRACT

A method of vibration treatment in at least one nasal cavity of a human subject is provided. The method includes the steps of: inserting a first stimulation member in a first nasal cavity; inserting a second stimulation member in a second nasal cavity; securing the first and second stimulation members such that the stimulation members are in fixed positions within the nasal cavities prior to vibration stimulation; arranging each of the first and second stimulation members to abut against tissue within each of the first and second nasal cavities at a first and second pressure; and imparting vibrations to tissue in at least one of the first and second nasal cavities via at least one of the first and second stimulation members.

15 Claims, 7 Drawing Sheets

(51) Int. Cl.
*A61H 1/00* (2006.01)
*A61H 9/00* (2006.01)
*A61H 23/02* (2006.01)
*G06F 19/00* (2011.01)

(52) U.S. Cl.
CPC ..... *A61H 23/04* (2013.01); *A61H 2201/0103* (2013.01); *A61H 2201/5071* (2013.01); *A61H 2205/023* (2013.01); *A61H 2230/045* (2013.01); *A61H 2230/065* (2013.01); *A61H 2230/105* (2013.01); *A61H 2230/505* (2013.01); *G06F 19/3481* (2013.01)

(58) Field of Classification Search
CPC ........ A61H 2230/065; A61H 2230/101; A61H 2201/123; A61H 2201/5071; A61N 1/0529; A61N 1/0534; A61N 2001/36039; A61N 1/36071; A61N 2001/36075; A61M 16/0683
See application file for complete search history.

(56) References Cited

U.S. PATENT DOCUMENTS

| | | | |
|---|---|---|---|
| 961,034 | A | 6/1910 | Siebert et al. |
| 1,735,519 | A | 11/1929 | Vance |
| 1,764,838 | A | 6/1930 | Horne |
| 2,052,321 | A * | 8/1936 | Smart ........................ 604/94.01 |
| 2,101,273 | A | 12/1937 | Smith |
| 3,055,371 | A * | 9/1962 | Kulick .................. A61M 25/02 600/546 |
| 3,209,755 | A | 10/1965 | McCarthy et al. |
| 3,612,211 | A | 10/1971 | Clark, III |
| 3,848,607 | A | 11/1974 | St. Clair |
| 4,373,523 | A | 2/1983 | Treutelaar |
| 4,462,411 | A | 7/1984 | Rickards |
| 4,593,688 | A | 6/1986 | Payton |
| 4,911,149 | A | 3/1990 | Borodulin et al. |
| 5,139,510 | A | 8/1992 | Goldsmith, III et al. |
| 5,193,534 | A | 3/1993 | Peppler |
| 5,609,606 | A | 3/1997 | O'Boyle |
| 5,682,881 | A | 11/1997 | Winthrop et al. |
| 5,755,225 | A * | 5/1998 | Hutson ............. A61M 16/0488 128/207.18 |
| 5,903,516 | A | 5/1999 | Greenleaf et al. |
| 6,159,170 | A | 12/2000 | Borodulin et al. |
| 6,193,680 | B1 | 2/2001 | Parsons et al. |
| 6,230,049 | B1 | 5/2001 | Fischell et al. |
| 6,358,272 | B1 | 3/2002 | Wilden |
| 6,684,883 | B1 | 2/2004 | Burns |
| 6,709,406 | B2 * | 3/2004 | Laserow ........................ 600/552 |
| RE41,376 | E | 6/2010 | Torch |
| 8,317,816 | B2 | 11/2012 | Becker |
| 9,579,247 | B2 * | 2/2017 | Juto ..................... A61H 9/0078 |
| 2001/0051819 | A1 | 12/2001 | Fischell et al. |
| 2002/0072781 | A1 | 6/2002 | Lattner et al. |
| 2002/0177889 | A1 | 11/2002 | Brisken et al. |
| 2003/0087734 | A1 | 5/2003 | Kring et al. |
| 2003/0116167 | A1 * | 6/2003 | Hooser ................. A61M 16/08 128/205.13 |
| 2003/0195578 | A1 * | 10/2003 | Perron et al. .................... 607/27 |
| 2004/0096089 | A1 * | 5/2004 | Borsook et al. ............. 382/131 |
| 2004/0097850 | A1 | 5/2004 | Plante |
| 2004/0138536 | A1 * | 7/2004 | Frei et al. ..................... 600/300 |
| 2004/0172112 | A1 | 9/2004 | Cioanta et al. |
| 2004/0220644 | A1 * | 11/2004 | Shalev et al. .................. 607/45 |
| 2004/0230252 | A1 | 11/2004 | Kullok et al. |
| 2004/0243172 | A1 | 12/2004 | Hogle |
| 2005/0011518 | A1 | 1/2005 | Biondo et al. |
| 2005/0021092 | A1 | 1/2005 | Yun et al. |
| 2005/0054958 | A1 | 3/2005 | Hoffmann |
| 2006/0081250 | A1 | 4/2006 | Bordewick et al. |
| 2006/0094992 | A1 | 5/2006 | Imboden et al. |
| 2006/0190022 | A1 | 8/2006 | Beyar et al. |
| 2007/0149905 | A1 | 6/2007 | Hanna |
| 2008/0027487 | A1 * | 1/2008 | Patel et al. ........................ 607/2 |
| 2008/0053457 | A1 * | 3/2008 | McDonald ............ A61M 16/06 128/207.17 |
| 2008/0198330 | A1 | 8/2008 | Taylor |
| 2008/0200848 | A1 | 8/2008 | Avni |
| 2008/0208168 | A1 | 8/2008 | Garabet |
| 2008/0243204 | A1 * | 10/2008 | Uthman et al. ................. 607/45 |
| 2008/0281238 | A1 | 11/2008 | Oohashi et al. |
| 2009/0005713 | A1 | 1/2009 | Podrazhansky et al. |
| 2009/0118786 | A1 | 5/2009 | Meadows et al. |
| 2009/0157141 | A1 * | 6/2009 | Chiao et al. .................... 607/46 |
| 2009/0187098 | A1 | 7/2009 | Makower et al. |
| 2010/0004709 | A1 | 1/2010 | Mische |
| 2010/0037897 | A1 * | 2/2010 | Wood ................ A61M 16/0683 128/207.11 |
| 2010/0094209 | A1 | 4/2010 | Drasler et al. |
| 2010/0228075 | A1 | 9/2010 | Lu |
| 2010/0234840 | A1 | 9/2010 | Jackson et al. |
| 2010/0249637 | A1 | 9/2010 | Walter et al. |
| 2010/0286576 | A1 | 11/2010 | Pryor et al. |
| 2010/0286626 | A1 | 11/2010 | Petersen et al. |
| 2010/0326434 | A1 | 12/2010 | Couts |
| 2011/0190668 | A1 | 8/2011 | Mishelevich |
| 2011/0270138 | A1 | 11/2011 | Mishelevich |
| 2013/0092173 | A1 | 4/2013 | Alexander et al. |

FOREIGN PATENT DOCUMENTS

| | | |
|---|---|---|
| FR | 592104 A | 7/1925 |
| FR | 838034 A | 2/1939 |
| FR | 920885 A | 4/1947 |
| GB | 385992 A | 1/1933 |
| GB | 1217760 A | 12/1970 |
| JP | 2001-17500 A | 1/2001 |
| JP | 2001-37883 A | 2/2001 |
| KR | 10-1019957 B1 | 3/2011 |
| RU | 2099039 C1 | 12/1997 |
| RU | 2199303 C1 | 2/2003 |
| SU | 1148614 A | 4/1985 |
| SU | 1560205 A1 | 4/1990 |
| WO | WO 86/01399 A1 | 3/1986 |
| WO | WO 96/36396 A2 | 11/1996 |
| WO | WO 96/39218 A1 | 12/1996 |
| WO | WO 01/41695 A2 | 6/2001 |
| WO | WO 2004/047675 A2 | 6/2004 |
| WO | WO 2004/105579 A2 | 12/2004 |
| WO | WO 2006/114783 A2 | 11/2006 |
| WO | WO 2008/138997 A1 | 11/2008 |
| WO | WO 2009/154457 A2 | 12/2009 |
| WO | WO 2010/033055 A1 | 3/2010 |

OTHER PUBLICATIONS

Alstadhaug, "Migraine and the Hypothalamus", Cephalalgia, 2009, pp. 1-9.

Ansarinia et al., "Electrical Stimulation of Sphenopalatine Ganglion for Acute Treatment of Cluster Headaches", Headache, Jul. 2010, pp. 1164-1174.

Bar-Shir et al., "Late Stimulation of the Sphenopalatine-Ganglion in Ischemic Rats: Improvement in N-Acetyl-Aspartate Levels and Diffusion Weighted Imaging Characteristics as Seen by MR", Journal of Magnetic Resonance Imaging, vol. 31, 2010, pp. 1355-1363.

Brown et al., "Towards a Physiology-Based Measure of Pain: Patterns of Human Brain Activity Distinguish Painful from Non-Painful Thermal Stimulation", Plos One, vol. 6, Iss. 9, e24124, Sep. 2011, pp. 1-8.

Kim et al., "Predicting the Timing of Spikes Evoked by Tactile Stimulation of the Hand", J Neurophysiol, vol. 104, 2010, pp. 1484-1496.

Krajnak et al., "Characterization of Frequency-Dependent Responses of the Vascular System to Repetitive Vibration", JOEM, vol. 52, No. 6, Jun. 2010, pp. 584-594.

Kuncel et al., "Selection of Stimulus Parameters for Deep Brain Stimulation", Clinical Neurophysiology, vol. 115, 2004, pp. 2431-2441.

(56) References Cited

OTHER PUBLICATIONS

Leroux et al., "Cluster Headache", Orphanet Journal of Rare Diseases, vol. 3, No. 20, 2008, 11 pages provided.
Ludwig, "The Velocity of Sound through Tissues and the Acoustic Impedance of Tissues", The Journal of the Acoustical Society of America, vol. 22, No. 6, Nov. 1950, 5 pages provided.
Malm, "Measurement of Nasal Patency", Allergy, vol. 52 (suppl. 40), 1997, pp. 19-23.
Malm, "Stimulation of Sympathetic Nerve Fibres to the Nose in Cats", Acta Otolaryng, vol. 75, 1973, pp. 519-526.
Salansky et al., "Responses of the Nervous System to Low Frequency Stimulation and EEG Rhythms: Clinical Implications", Neuroscience and Biobehavioral Reviews, vol. 22, No. 3, 1998, pp. 395-409.
Tepper et al., "Acute Treatment of Intractable Migraine With Sphenopalatine Ganglion Electrical Stimulation", Headache, vol. 49, Jul. 2009, pp. 983-989.
VBM, "VBM Tube Fixations", VBM Medizintechnik GmbH, 2006, 6 pages provided.
Zelena, "Nerves and Mechanoreceptors: The Role of Innervations in the Development and Maintenance of Mammalian Mechanoreceptors", Springer, 1994, pp. 147-148.
U.S. Appl. No. 13/714,643, filed Dec. 14, 2012.
U.S. Appl. No. 13/714,636, filed Dec. 14, 2012.
U.S. Appl. No. 13/714,726, filed Dec. 14, 2012.
U.S. Appl. No. 13/714,649, filed Dec. 14, 2012.
U.S. Appl. No. 13/714,612, filed Dec. 14, 2012.
Klinger et al., "Untersuchungen zur Mikro-zirkulation der Nasenschleimhaut bei Verwendung von Ballon-tamponaden", Laryngo-Rhino-Otol., vol. 76, 1997, pp. 127-130, XP008066107.

\* cited by examiner

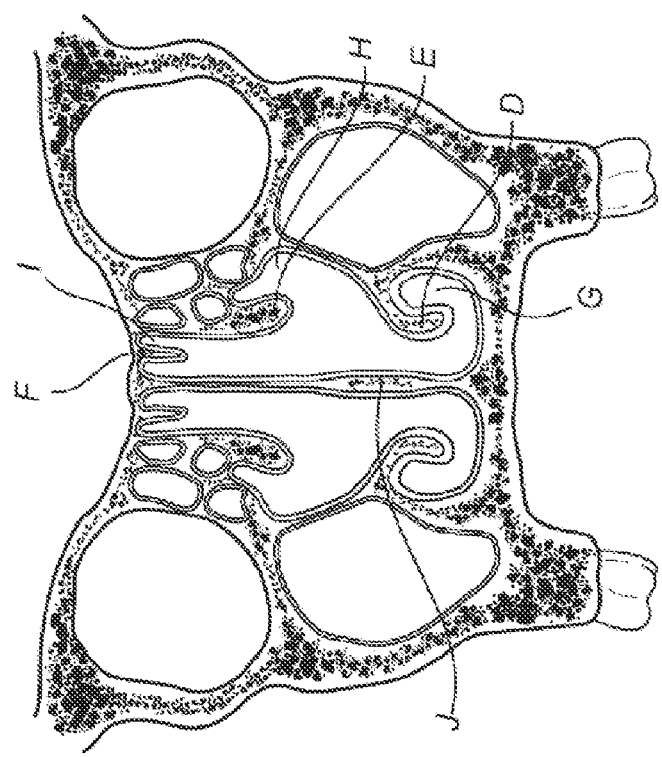
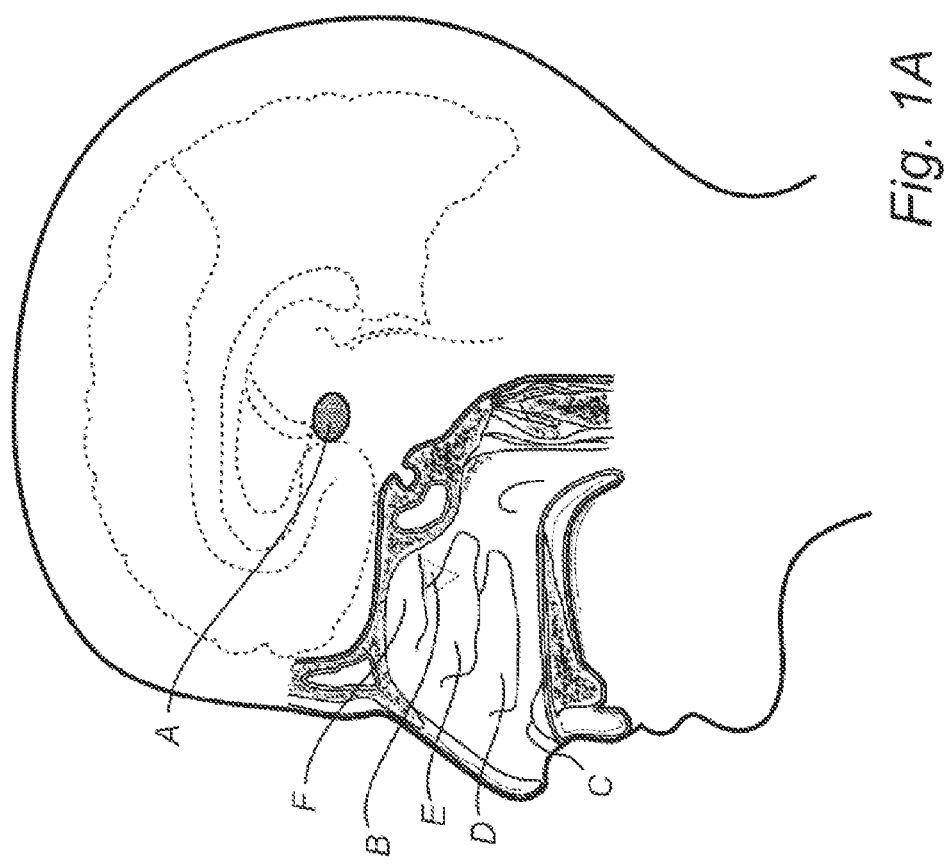
Fig. 1A
Fig. 1B

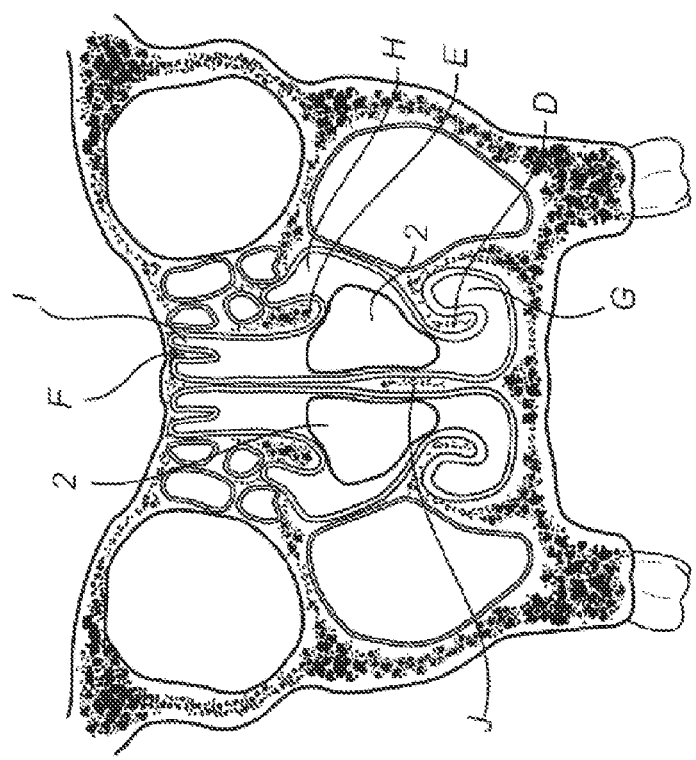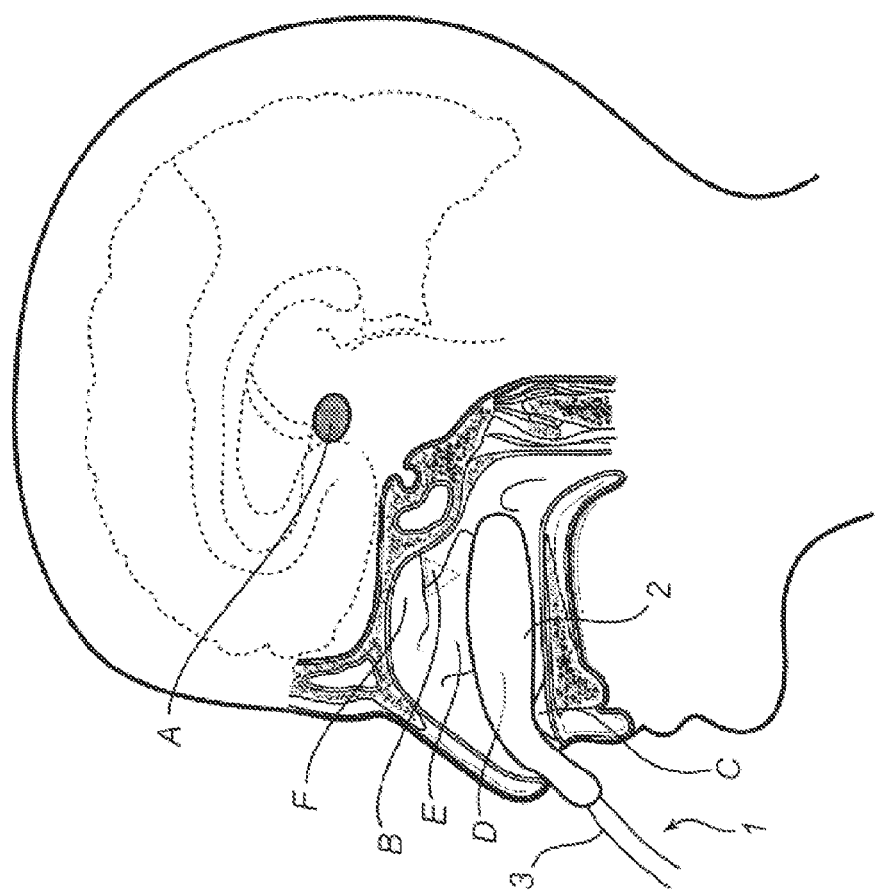
Fig. 3A
Fig. 3B

DOUBLE STIMULATION

CROSS-REFERENCE TO RELATED APPLICATIONS

This application claims priority under 35 U.S.C. §119(e) to U.S. Provisional Application No. 61/576,782 filed on Dec. 16, 2011. This application also claims priority under 35 U.S.C. §119(a) to Application No. 11194068.0, filed in Europe on Dec. 16, 2011. The entirety of each of the above-identified applications is expressly incorporated herein by reference.

BACKGROUND OF THE INVENTION

1. Field of the Invention

The present invention relates to devices and methods for vibration stimulation in at least one nasal cavity of a human subject, wherein a first and a second stimulation member are arranged to abut against tissue in the nasal cavities and to impart vibrations to said tissue in at least one nasal cavity.

2. Description of Background Art

Sphenopalatine ganglion is a parasympathetic ganglion found in the pterygopalatine fossa. It is one of four parasympathetic ganglia of the head and neck. It has the largest aggregate of neurons in the head outside of the brain. The sphenopalatine ganglion has been associated with a wide variety of pain problems that range from pain in the head and neck to pain of the low back. For example, electrical stimulation of the sphenopalatine ganglion has been shown to relieve acute severe cluster headache pain (Ansarinia et al, *Headache;* 2010, 50:1164-1174). In other examples, blocking of the sphenopalatine ganglion has been successful for reducing pain associated with headache.

The hypothalamus is a portion of the brain which lies beneath the thalamus and which contains a number of small nuclei with a variety of functions. One of the most important functions of the hypothalamus is to provide a link between the nervous system and the endocrine system via the pituitary gland (hypophysis). Several illnesses are associated with dysfunction in the hypothalamus, such as migraine, Ménière's disease, hypertension, cluster headache, arrhythmia, ALS, irritable bowel syndrome, sleep disorders, diabetes, obesity, multiple sclerosis, tinnitus, Alzheimer's disease, mood and anxiety disorders and epilepsy. In many cases the connection between the hypothalamus and the condition in question is not fully understood.

Cluster headache (CH), also called Horton's headache, is the most severe primary headache disorder. The disease is characterized by recurrent short-lasting attacks of torturous unilateral periorbital pain, mostly accompanied by ipsilateral autonomic signs such as nasal congestion, ptosis, lacrimation and redness of the eye. New surgical therapies have been tested. However, these treatments are invasive and can cause severe complications. The pathophysiology of CH is currently unknown, but involvement of the hypothalamus and the parasympathetic nervous system has been proposed (Leoux E et al, *Orphanet J of Rare Diseases;* 2008, 3:20).

Heart rhythm problems (heart arrhythmias) occur when the electrical impulses in the heart that coordinates the heartbeats do not work properly, causing the heart to beat too fast, too slow or irregularly. Heart arrhythmias are often harmless. Most people have occasional, irregular heartbeats that may feel like a fluttering or racing heart. However, some heart arrhythmias may cause bothersome, sometimes even life-threatening, signs and symptoms. Treatment form depends on the type and seriousness of the arrhythmia. Some people having the condition require no treatment. For others, treatment can include medication, making lifestyle changes and undergoing surgical procedures. A proposed reason for arrhythmias is a so called sympathetic imbalance, i.e. an imbalance in the sympathetic part of the autonomic nervous system, the heart rate is controlled by the hypothalamus via the vagus nerves so it seems plausible that such an imbalance is connected to hypothalamic activity.

There are several known devices for conducting treatments with systemic effects in human subjects. Devices for use in for example the nasal cavity often aim at achieving a local effect, such as decongesting the nasal mucosa, and may often be used in combination with a chemical substance. One example of a device for achieving a local effect on the nasal mucosa is disclosed in WO 2008/138997.

Devices are also known that by mechanical vibration affect tissue in a body cavity, e.g. in the ear or over a body surface. In US 2008/281238, a system for increasing activity on the fundamental brain is disclosed. The disclosed system comprises a first and a second vibration applying device, wherein the first vibration applying device applies vibrations having frequency components within an audible range to the auditory sense system of a living body. The second vibration applying device applies vibrations having super-high frequency components exceeding the audible range to another region than the auditory sense system, such as the nasal cavity.

In RU 2199303 there is disclosed a method of treating the neuroautonomic form of vasomotor rhinitis. More specifically, the method involves vibratory massage of the anterior third of the inferior and middle conchae at a frequency of 50 Hz for 1.5-2 minutes in combination with vibratory massage of certain biological active points (BAP:s) located in the hand, chin and near the nose. The instrument used for delivering the vibratory massage is described as a vibromassage instrument having a ball and a tip.

In US 2011/190668, methods and systems for non-invasive neuromodulation of the sphenopalatine ganglion is disclosed. An ultrasound transducer to treat migraine and cluster headache is described. An acoustic frequency, e.g. 0.44 MHz (typically in the range of 0.3 to 0.8 MHz), which permits the ultrasound to effectively penetrate through bone, is used.

SUMMARY OF THE INVENTION

It is an object of the present invention to provide novel devices and methods for vibration stimulation in one or both nasal cavities of a human subject.

Another object of the present invention is to provide novel devices and methods for vibration stimulation for treating diseases related to dysfunction of the sphenopalatine ganglion and/or the hypothalamus.

Yet another object of the present invention is to provide novel devices and methods for treating migraine, cluster headache and heart arrhythmia.

There is, in a first aspect of the present invention, provided a device for vibration stimulation in at least one nasal cavity of a human subject, comprising a first stimulation member arranged to be introducible into a first nasal cavity, to be expanded within the first nasal cavity and to abut against tissue in the first nasal cavity;

a first expansion member arranged to expand the first stimulation member; the first expansion member comprising a first tubular structure arranged at least partly within the first stimulation member, wherein the first tubular structure is provided with a plurality of openings arranged for fluid communication with the stimulation member;

a second stimulation member arranged to be introducible into a second nasal cavity, to be expanded within the second nasal cavity and to abut against tissue in the second nasal cavity, and a second expansion member arranged to expand the second stimulation member; the second expansion member comprising a second tubular structure arranged at least partly within the second stimulation member, wherein the second tubular structure is provided with a plurality of openings arranged for fluid communication with the second stimulation member;

wherein at least one of the first and second stimulation members is arranged to impart vibrations to the tissue in at least one nasal cavity.

By using a device according to the present invention with two stimulation members, the total stimulation time for vibration stimulation in the nasal cavities of a human subject may be reduced compared to the total stimulation time for using only one stimulation member. The introduction of two stimulation members into one nasal cavity each, eliminates the need to move one stimulation member between the two nasal cavities during vibration stimulation.

Another advantage with a device according to the present invention over a device with only one stimulation member is a reduction of discomfort for the human subject and a decreased work load for an operator during vibration stimulation of both nasal cavities. If only one stimulation member was used this would have to be removed and be re-inserted (possibly several times) during vibration stimulation, whereas in the present case vibration stimulation can alternate between the two nasal cavities without any additional efforts.

By using a device with two stimulation members, the vibration stimulation can be performed either simultaneously in both nasal cavities or sequentially in one nasal cavity at a time.

Vibration stimulation with the two stimulation members can be performed in a controlled fashion. The selection of vibration stimulation scheme, i.e. simultaneous vibrations in both nasal cavities or sequential vibrations in one nasal cavity at a time, may be performed manually by either an operator, such as a doctor, or by the human subject himself/herself during stimulation. For example, the human subject can easily switch stimulation cavity by selecting which stimulation member that should vibrate. In another example, a system using a device according to the present invention, and comprising for example a data collection module and an analyzing module, can determine based on analysis of a bodily response, when the vibration stimulation should be switched between the two nasal cavities and when the vibration stimulation should be terminated.

Several vibration stimulation schemes can be selected using a device comprising two stimulation members. For example, the two stimulation members may impart vibrations at the same frequency or at different frequencies. In another example, each of the two stimulation members may abut against the tissue of a nasal cavity at the same pressure or different pressures.

Vibration stimulation in at least one nasal cavity of a human subject can moreover be used in order to affect the sphenopalatine ganglion. Studies have shown that the sphenopalatine ganglion may be associated with a wide variety of pain problems. By stimulating the sphenopalatine ganglion with vibrations, diseases associated with a dysfunction of the sphenopalatine ganglion can be affected and the symptoms, such as pain, can be reduced.

Additionally, vibration stimulation can be used to affect the hypothalamus. By stimulating the hypothalamus with vibrations, diseases associated with a dysfunction of the hypothalamus can be affected and the symptoms of the diseases can be reduced.

By selecting two possibly different frequencies, to be applied either simultaneously or sequentially, and by selecting two possibly different pressures at which the stimulation members abut against the tissue in the two nasal cavities, vibration stimulation of at least one biological target, such as the hypothalamus and/or the sphenopalatine ganglion, can be provided. By controlling the vibration stimulation parameters frequency, amplitude, pressure and vibration stimulation duration, treatment of various diseases associated with e.g. a dysfunction of the hypothalamus and/or the sphenopalatine ganglion can be performed. It seems preferable to use comparatively lower pressures and/or frequencies to affect the sphenopalatine ganglion than to affect the hypothalamus.

The device according to the present invention is arranged to impart vibrations to the tissue in at least one nasal cavity. More specifically, the device of the first aspect of the present invention may be arranged to impart vibrations to bone structures in at least one nasal cavity, such as to parts of the inferior, middle and/or superior concha(e). Thus, the device may mechanically transmit vibrations via bone structures connected to the cranium to for example the hypothalamus. In another example, the device may mechanically transmit vibrations via bone structures to the sphenopalatine ganglion. In yet another example, the device is arranged close to the sphenopalatine ganglion and may impart vibrations directly to the sphenopalatine ganglion. The human body has different cell types to detect and communicate mechanical influence, so called mechanoreceptors. It is conceivable that the frequency(s) of the vibration stimulation can be tuned to match the response of some of the mechanoreceptors to obtain a desired therapeutic effect on a biological target, such as the hypothalamus and the sphenopalatine ganglion.

The signal paths between the brain and heart are asymmetric, hence a vibration stimulation scheme comprising for example sequential vibrations in the nasal cavities could be a way to fine tune the effect in human subjects suffering from for example hypertension and heart arrhythmia.

Thus, in one embodiment, said first stimulation member is arranged to impart vibrations to the tissue of the first nasal cavity and said second stimulation member is arranged to impart vibrations to the tissue of the second nasal cavity. In one example, vibrations are firstly imparted by the first stimulation member during a period of time while the second stimulation member is preferably inactive. The vibration stimulation in the first nasal cavity, as imparted by the first stimulation member, can be terminated in a controlled fashion. Vibrations can then be imparted by the second stimulation member to the other nasal cavity while the first stimulation member is preferably inactive.

In another embodiment, at least one of said stimulation members comprises a pressure sensor. When using a stimulation member comprising a pressure sensor for measuring a pressure inside a nasal cavity, the stimulation member can be arranged to at least partly abut against the tissue in the nasal cavity. For example, the pressure exerted on the first stimulation member by the tissue of the first nasal cavity can be measured when the first stimulation member comprises a pressure sensor. In another example, the second stimulation member can comprise a pressure sensor and the pressure which is exerted by the tissue in the second nasal cavity on the second stimulation member can be measured. In yet another example, each of the stimulation members can comprise a pressure sensor, and hence two pressures can be measured, as exerted by the tissue in the nasal cavities on each of the stimulation members.

In one embodiment, the device comprises at least one anchoring member arranged to secure said first and second stimulation members in fixed positions in the first and second nasal cavities during vibration stimulation in at least one nasal cavity. By using at least one anchoring member the two stimulation members can be held in fixed positions relative the nasal cavities and also relative each other. In the context of the present invention, an anchoring member can be selected from the group consisting of: a helmet, a headband, a facial mask and a pair of glasses. In another embodiment, the device further comprises at least one adjustment member for adapting the at least one anchoring member to individual variations between human subjects. In the context of the present invention, an adjustment member can be selected from the group consisting of: a snap wheel, a strap which is preferably elastic, and a locking member. A person skilled in the art understands which anchoring members and adjustments members can be used for securing the two stimulation members in fixed positions during vibration stimulation in the at least one nasal cavity of a human subject.

In one embodiment, the device comprises at least one vibration generating member connectable to said first and second stimulation member, optionally via the first and second expansion member, wherein the at least one vibration generating member is arranged to bring at least one of said first and second stimulation members to vibrate. In another embodiment, the first stimulation member is connectable to a first vibration generating member and the second stimulation member is connectable to a second vibration generating member wherein the first and the second vibration generating member are arranged to bring the first and the second stimulation member to vibrate. Thus, the device may comprise two vibration generating members, each of them being connectable to one stimulation member. In the context of the present invention, the at least one vibration generating member can for example be controlled by an applied electrical voltage supplied from a control unit. In such examples, the vibration generating member may be arranged within a stimulation member. In other examples, the vibration generating member is externally arranged. Such an external vibration source, for example a transducer, may be arranged so as to supply vibrations to a fluid contained within a stimulation member. In embodiments where the device comprises one vibration generating member, the device may further comprise a valve for controlling the supply of vibrations to each of the stimulation members.

In one embodiment, each one of said first and second stimulation members is arranged to impart vibrations at at least one frequency selected from the range of between 40 Hz and 100 Hz to each of the first and second nasal cavities. Thus, it should be understood that vibration stimulation may be performed at one selected frequency, e.g. 68 Hz, or at several frequencies within a predetermined frequency interval, such as between approximately 50 Hz and 80 Hz, such as between approximately 50 Hz and 75 Hz, such as between approximately 50 Hz and 70 Hz, such as between approximately 55 Hz and 75 Hz, such as between approximately 60 Hz and 75 Hz, and such as between approximately 60 Hz and 70 Hz. Consequently, during vibration stimulation the two frequencies may be constant or be changed for example manually by an operator, such as a doctor, by the human subject himself/herself, or by a system.

The first stimulation member is, in another embodiment, arranged to impart vibrations at a different frequency than the second stimulation member. The difference between the frequencies imparted by said first stimulation member and said second stimulation member is in the range of 5-30 Hz, such as in the range of 10-20 Hz. Due to the long wavelength in body tissue, application of different frequencies in the two nasal cavities will result in an average frequency being applied to the tissue with a modulated amplitude.

Examples of a first and a second amplitude is in the range of between approximately 0.05 mm and 20 mm. Suitable amplitude(s) depend(s) on the nasal anatomy of the particular human subject.

Each of the stimulation members can be arranged in an essentially non-expanded state such as to facilitate introduction into the nasal cavities of a human subject. When the stimulation members are secured in fixed positions in the nasal cavities, the stimulation members can be expanded to a volume such as to provide a direct contact with the surrounding tissue in the nasal cavities. In one embodiment, the device comprises at least one expansion member arranged to expand at least one of said first and second stimulation member. In one example, one expansion member can provide expansion of the two stimulation members. In another embodiment, a first expansion member can be arranged to expand the first stimulation member and a second expansion member can be arranged to expand the second stimulation member. In the context of the present invention, the expansion can be accomplished by means of a fluid supplied to the stimulation members, accordingly arranged to encompass such fluid. When the stimulation members are expanded inside the nasal cavities, one of or both of the stimulation members can be brought to vibrate by means of the at least one vibration generating member, optionally via said first and second expansion member.

In one embodiment, each of said first and second stimulation members is arranged to abut against the tissue of each of the first and second nasal cavities, at at least one pressure selected from the range of between approximately 20 mbar and 120 mbar. Thus, each of the stimulation members may provide direct contact with the tissue of a nasal cavity. Moreover, the stimulation members can be arranged to abut against the tissue of the first and second nasal cavities at a pressure of between approximately 50 mbar and 120 mbar, such as for example between approximately 70 mbar and 110 mbar, such as for example between approximately 75 mbar and 100 mbar, and such as between approximately 90 mbar and 105 mbar. In one example, the first pressure is in the range of between approximately 20 mbar and 50 mbar and the second pressure is in the range of between 70 and 120 mbar. During vibration stimulation the pressure can be constant or be changed for example by the human subject himself/herself, by an operator, such as for example a doctor, or by a system. Thus, it should be understood that the pressure between the tissue of the first nasal cavity and the first stimulation member can be the same as or different from the pressure between the tissue of the second nasal cavity and the second stimulation member. The size and shape of the nasal cavities may differ in a particular human subject or between different human subjects, and hence the stimulation members may have to be expanded to different relative volumes in order to reach the same pressures within the nasal cavities.

The first and second tubular structure of the expansion member is provided with a plurality of openings for fluid communication with the interior of the stimulation member. Expansion of the first and second stimulation members may be accomplished by means of a fluid independently distributed to the first and second stimulation members via the first and second expansion member. Due to the complex anatomy of the nasal cavity, there might be obstructions somewhere along the length of the stimulation member. The plurality of openings prevents irregular expansion due to anatomical obstructions and ensures that each stimulation member is expanded accordingly when positioned in the nasal cavity. The plurality of openings moreover provides the tubular structure with flexibility which facilitates correct insertion and positioning of the stimulation member in the part of the nasal cavity to be treated.

In one embodiment, the first tubular structure has a bending stiffness in a first direction perpendicular to a first longitudinal direction of the first tubular structure that is different from a bending stiffness in another direction perpendicular to the first direction and perpendicular to the first longitudinal direction of the first tubular structure. The tubular structure of this embodiment is thus sufficiently resilient, and at the same time sufficiently pliable, in order to follow the, sometimes irregular, shape of the nasal cavity. At the same time, accidental bending of the tubular structure during the introduction into the nose is avoided. In one embodiment, the second tubular structure has a bending stiffness in a second direction perpendicular to a second longitudinal direction of the second tubular structure that is different from a bending stiffness in another direction perpendicular to the second direction and perpendicular to the second longitudinal direction of the second tubular structure.

In one embodiment, the first tubular structure comprises one opening at one end, the one opening being arranged freely within and in fluid communication with the first stimulation member. Such a free arrangement of the end may facilitate preservation of a smooth surface of the stimulation member, by avoiding protruding parts in the stimulation member that may harm the sensitive tissue in the nasal cavity. The end opening may further accomplish expansion of parts of the stimulation member located in posterior, and thus narrow, parts of the nasal cavity. In one embodiment, the second tubular structure comprises one opening at one end, the one opening being arranged freely within and in fluid communication with the second stimulation member.

In one embodiment, a distance from the one end of the first tubular structure of the first expansion member to an inner wall of the first stimulation member is in the range of from 1 to 10 mm. In one embodiment, a distance from the one end of the second tubular structure of the second expansion member to an inner wall of the second stimulation member is in the range of from 1 to 10 mm.

In one embodiment the plurality of openings of the first tubular structure is distributed along a first longitudinal direction of the first tubular structure. In one embodiment, the plurality of openings of the second tubular structure is distributed along a second longitudinal direction of the second tubular structure.

In one embodiment, the plurality of openings are arranged alternately on opposite side portions of the first tubular structure along the first longitudinal direction, wherein a first cross section of the first tubular structure perpendicular to the first longitudinal direction intersect only one opening of either side of the first tubular structure. In one embodiment, the plurality of openings are arranged alternately on opposite side portions of the second tubular structure along the second longitudinal direction, wherein a second cross section of the second tubular structure perpendicular to the second longitudinal direction intersect only one opening of either side of the second tubular structure.

In one embodiment, the number of openings distributed along a first longitudinal direction of the first tubular structure is between 4 and 6. In one embodiment, the number of openings distributed along a second longitudinal direction of the second tubular structure is between 4 and 6. Each of the openings from the plurality of openings may have a shape selected from elliptical and circular cutouts.

In one embodiment, each of the openings independently has a size in the range of from 1 to 5 mm.

In one embodiment, the first tubular structure has an outer diameter in the range of from 1 to 5 mm. A diameter of 5 mm or less may further facilitate introduction of the stimulation member into the nostril and nasal cavity and positioning within parts of the nasal cavity to be treated with vibration stimulation. In one embodiment, the second tubular structure has an outer diameter in the range of from 1 to 5 mm.

In one embodiment, the part of said first tubular structure being arranged within the first stimulation member is between 40 and 60 mm in length. This length of the tubular structure may further facilitate insertion and positioning of the stimulation member in the posterior part of the nasal cavity. In one embodiment, the part of said second tubular structure being arranged within the second stimulation member is between 40 and 60 mm in length.

In one embodiment, the first expansion member further comprises a first elongated structure arranged in fluid communication with the first tubular structure. In one embodiment, the second expansion member further comprises a second elongated structure arranged in fluid communication with the second tubular structure.

In one embodiment, the first expansion member comprises at least one channel arranged for fluid communication with the first stimulation member, such as for supplying fluid to the first stimulation member. In embodiments where the expansion member comprises a tubular structure and an elongated structure, the channel fluidly connects the two structures with each other and with an interior of the stimulation member. In one embodiment, the second expansion member comprises at least one channel arranged for fluid communication with the second stimulation member, such as for supplying fluid to the second stimulation member.

In one embodiment, the first elongated structure is tubular and has a diameter that is between 2 to 4 times the diameter of the first tubular structure. The tubular structure is the part of the expansion member that, since it resides within the stimulation member, will be positioned mainly in the nasal cavity during vibratory stimulation. It may thus conveniently have a smaller diameter than the elongated structure, which correspondingly is the part of the expansion member that will be positioned mainly outside of the nasal cavity. In one embodiment, the second elongated structure is tubular and has a diameter that is between 2 to 4 times the diameter of the second tubular structure.

In one embodiment, a part of the first elongated structure is arranged within the first stimulation member, the length of the part being selected from a length within the range of from 5 to 15 mm. This part of the elongated structure may enclose an ending of the tubular structure, preferably an end portion of the tubular structure. The stimulation member arranged around this part of the elongated structure may preferably expand only to a small extent when the device is in use. In one embodiment, a part of the second elongated structure is arranged within the second stimulation member, the length of the part being selected from a length within the range of from 5 to 15 mm.

In one embodiment, the device comprises two stimulation members each independently selected from a plurality of stimulation members which are geometrically different. The plurality of stimulation members may for example differ in shape as well as in length, width and/or diameter. By selection and use of two different stimulation members from a plurality of stimulation members, any influence differences in nasal anatomy may have on vibration stimulation is reduced.

There is in other device aspects of the invention, provided a device for vibration stimulation in at least one nasal cavity of a human subject, comprising a first stimulation member and a second stimulation member, wherein said first stimulation member is introducible into a first nasal cavity and said second stimulation member is introducible into a second nasal cavity and said first and second stimulation members are arranged to abut against tissue and to impart vibrations to said tissue in at least one nasal cavity In another aspect, there is provided a system for vibration stimulation in at least one nasal cavity of a human subject, comprising:

a device according to the device aspects of the present invention; and at least one of a frequency regulating module arranged to adjust the frequency(s) of the vibrations imparted by one of or both of the first and second stimulation member(s) of said device to one of or both of the first and second nasal cavities(s);

an amplitude regulating module arranged to adjust the amplitude(s) of the vibrations imparted by one of or both of the first and second stimulation member(s) of said device to one of or both of the first and second nasal cavities(s); and a pressure regulating module arranged to adjust the pressure(s) at which one of or both of the first and second stimulation member(s) of said device abut(s) against the tissue of one of or both of the first and second nasal cavities(s).

It should be understood that the embodiments enclosed in relation to other aspects of the present invention are, where applicable, relevant also to the system aspect of the invention. Thus, the system may for example comprise a device according to different examples as defined in relation to the device aspect.

In a system according to the second aspect, at least one of the vibration stimulation parameters of frequency, amplitude and abutting pressure may be independently regulated. Exemplary ranges for frequency, amplitude and pressure are disclosed in connection with the device aspect. The regulating modules of the system may be controlled manually by an operator or by the human subject himself/herself, or alternatively, by means of a control unit.

The system further comprises, in one embodiment, a data collection module arranged to obtain and store data time samples comprising an input signal reflecting a measure of a bodily response to vibration stimulation together with at least one associated vibration stimulation parameter selected from: the frequency of the vibrations imparted by one of or both of the first and second stimulation member(s); the amplitude of the vibrations imparted by one of or both of the first and second stimulation member(s); the pressure at which one of or both of the first and second stimulation member(s) abut(s) against the tissue of one of or both of the first and second nasal cavities(s); the difference between the frequencies of the vibrations imparted by the first and second stimulation members; the difference between the amplitudes of the vibrations imparted by the first and second stimulation members; the difference between the pressures at which the first and second stimulation members abut against the tissue of the first and second nasal cavities, and a vibration stimulation duration.

In one embodiment, the system further comprises an analyzing module arranged to analyze the stored input signal in order to determine if a desired value of the measure is approached, wherein, if the desired value is not approached, the analyzing module is arranged to instruct at least one of the frequency regulating module, the amplitude regulating module and the pressure regulating module to adjust at least one vibration stimulation parameter as defined above, by way of one of a random adjustment; an adjustment calculated from a pre-programmed look-up table comprising correlations between desired changes in the measure of bodily response and at least one vibration stimulation parameter, and an adjustment calculated based on correlations between desired changes in the measure of bodily response and at least one vibration stimulation parameter as derived from the previously stored data time samples. Deriving correlations from previously stored data may comprise identifying periods wherein the value of the bodily response has been of roughly constant and an adjustment of one or more of the vibration stimulation parameters has been done causing a change in the bodily response. From such events, a correlation between adjustment of vibration stimulation parameters and changes input signal may be identified. One example of a correlation may be a decrease bodily response caused by a raised frequency. An exemplary way to store these correlations would be in a database where required adjustments of the vibration stimulation parameters can be looked up given current bodily response, desired change (e.g. increase or decrease) of the bodily response, and current vibration stimulation parameters. A database containing this type of data can be supplied to the system, e.g. in the form of a look-up table. In the latter case the system can be somewhat simplified since the means needed to derive correlations can be omitted. Although random adjustments are straightforward to implement and may give the desired change in bodily response, it can also be an inefficient way to find vibration stimulation parameters when compared to the more systematical ways of finding suitable adjustments.

In one embodiment, the desired value of the measure of the bodily response is proportional to a measure of the bodily response previously obtained during the vibration stimulation. A non-limiting example is a case where an initial response to the stimulation is recorded, during say the first two minutes, and the desired value is e.g. twice the recorded value.

In one embodiment the desired value is set to a fraction of an initial measured value, i.e. a value obtained prior to the start of vibration stimulation, or to a pre-programmed desired value, for example a value of the bodily response normally recorded in healthy humans.

The difference between the frequency of the vibrations imparted by the first stimulation member and the frequency of the vibrations imparted by the second stimulation member may be in the range of between approximately 5 Hz and 30 Hz, such as between approximately 10 Hz and 20 Hz. The difference between the amplitude of the vibrations imparted by the first stimulation member and the amplitude of the vibrations imparted by the second stimulation member may be in the range of between approximately 0.05 mm and 1.5 mm. The difference between the pressure at which the first stimulation member abuts against the tissue of the first nasal cavity and the pressure at which the second stimulation member abuts against the tissue of the second nasal cavity may be in the range of between approximately 5 mbar and 100 mbar, such as between approximately 10 mbar and 80 mbar, such as between approximately 20 mbar and 50 mbar.

The measure of a bodily response may be used as an input signal not only for adjusting at least one vibration stimulation parameter for vibration stimulation by one of or both of the stimulation members, but also for determining whether the vibration stimulation should be terminated or if the vibration stimulation cavity (i.e. in the case of sequentially imparting vibrations to the first and the second nasal cavity) should be switched.

The input signal reflecting a measure of a bodily response corresponds, in one embodiment, to the pressure between the tissue of the first nasal cavity and the first stimulation member or between the tissue of the second nasal cavity and the second stimulation member. In similarity to the device aspect of the present invention, one of or both of the stimulation members may comprise a pressure sensor capable of measuring the pressure exerted by the tissue in one nasal cavity when the stimulation member abuts against the tissue.

The input signal reflecting a measure of a bodily response is, in another embodiment, selected from the group consisting of: oxygen consumption as measured by functional Magnetic Resonance Imaging (fMRI), metabolic activity as measured by Positron Emission Tomography (PET), magnetic signals as measured by magnetoencephalography (MEG), electrical signals as measured with electroencephalography (EEG), electrocardiogram (ECG), pain sensation, heart rate, pupil size, body temperature, photoplethysmogram, and blood pressure. It is anticipated that new and improved methods and devices will be developed within the field of functional neuroimaging and that they will be possible to use in aspects of the present invention. In the context of the present invention, functional neuroimaging refers to methods and devices comprising fMRI, PET, and MEG.

The input signal reflecting a measure of a bodily response may directly or indirectly reflect the activity of a biological target, such as the hypothalamus and/or the sphenopalatine ganglion. Examples of direct measures of bodily responses include signals derived from functional neuroimaging methods and devices, such as fMRI, PET, and MEG. Examples of indirect measures of bodily responses include heart rate, pupil size, body temperature, photoplethysmogram, and blood pressure.

Pain sensation can be estimated using a visual analogue scale (VAS). The human subjects can estimate their pain before and after vibration stimulation on a scale from 1 to 10, wherein 0 corresponds to no pain and 10 corresponds to maximal pain.

Photoplethysmogram can be obtained by using a photoplethysmography sensor which can be attached to an ear lobe of the human subject during vibration stimulation. The photoplethysmography sensor may be used to measure the oxygen saturation of the blood.

To diagnose a heart arrhythmia, heart-monitoring tests specific to arrhythmias may be performed. These may include an electrocardiogram (ECG). During an ECG, sensors (electrodes) capable of detecting the electrical activity of the heart are attached to the human subject's chest and sometimes to the human subject's limbs. An ECG measures the timing and the duration of each electrical phase of the human subject's heartbeat. By using for example an ECG, the heartbeats can be monitored during vibration stimulation. The ECG may for example be used for determining whether the vibration stimulation should be terminated.

The device of said system may, in one example, comprise an anchoring member in the form of a pair of glasses. The pair of glasses may comprise a member, such as a scale, for measuring the pupil size of the human subject.

In another example, the device may comprise an anchoring member with EEG electrodes for measuring electric signals, such as brain activity, of the human subject.

The system further comprises, in another embodiment, a monitoring device arranged to monitor a measure of e.g. the activity of a biological target, such as the hypothalamus and/or the sphenopalatine ganglion. The monitoring device may provide real-time monitoring of a direct measure, such as by means of functional neuroimaging, or an indirect measure, such as by means of a bodily response such as e.g. pupil size or heart activity.

In yet another embodiment, the analyzing module is arranged to terminate vibration stimulation or to initiate switching of vibration stimulation cavity when the measure of bodily response has reached a threshold value. The threshold value can be predetermined or calculated, in absolute or relative terms. For example, the threshold value may be defined relatively or absolutely as corresponding to the level of activity in parts of the tissue surrounding for example the hypothalamus and/or the sphenopalatine ganglion. The analyzing module thus compares the input signal to a threshold value and may issue a command to terminate the vibration stimulation in one or both nasal cavities when the threshold value is reached. Thus, reaching of the threshold value represents the attainment of a desired level of vibration stimulation of for example the hypothalamus and/or the sphenopalatine ganglion and indicates that the stimulation may either be terminated or the vibration stimulation cavity, in cases where vibrations are imparted sequentially in the two nasal cavities, may be switched. Thus, the vibration stimulation in a first nasal cavity may have reached a saturation level where further vibration stimulation in the same nasal cavity is of no further benefit to the human subject. In such a case, vibration stimulation may be continued in the second nasal cavity of the human subject.

In some embodiments of the system aspect, the system further comprises a control unit which in turn may comprise, where applicable, the data collection module, a data processing module and the analyzing module.

It should be understood that embodiments and examples described in relation to the device and system aspects of the present invention are equally relevant, when applicable, to the following method aspects of the present invention.

In another aspect, there is provided a method of preparing vibration stimulation in at least one nasal cavity of a human subject comprising the steps of:

a) inserting a first stimulation member of a device according to the device aspect of the present invention in a first nasal cavity;

b) inserting a second stimulation member of said device in a second nasal cavity;

c) securing said first and second stimulation members such that the stimulation members are in fixed positions within the nasal cavities prior to vibration stimulation;

d) arranging each one of the first and second stimulation members to abut against tissue within each one of the first and second nasal cavities at a first and second pressure, and e) selecting a first and optionally a second frequency for administration to tissue via at least one of said first and second stimulation member.

Each of the first and second stimulation members is positioned and secured within a nasal cavity, optionally using at least one anchoring member and at least one adjustment member. Variations between human subjects may be adjusted for by using the anchoring member(s) and the adjustment member(s) for better adaptation to the human subject in question.

The first and second stimulation members are thereafter expanded within the first and second nasal cavities. Following expansion, a first and optionally a second frequency is/are selected.

Based on theoretical estimations and/or previously collected data from vibration stimulation, for example from vibration stimulation of the sphenopalatine ganglion according to the present invention, the method of preparing vibration stimulation may provide e.g. improved positioning of the first and second stimulation members in the nasal cavities and thereby improved transferring of vibrations to the treatment area, for example the sphenopalatine ganglion. The same reasoning is valid for vibration stimulation of other treatment targets, such as for example the hypothalamus.

The method of preparing vibration stimulation can provide preparation and selection of a treatment regime for a particular human subject. The preparative method may aim at preparing a first and only round of treatment for a particular human subject, or a second or further round of treatment. If the method concerns preparing a second or further round of treatment for a particular human subject, the data, such as the measure of a bodily response and the vibration stimulation parameters used, collected during the previous round of treatment may form basis for selection of vibration stimulation parameters for the second or further round of treatment.

The preparative method may moreover comprise selecting a first and optionally a second treatment area within at least one nasal cavity. The treatment areas within the two nasal cavities may be selected such as to maximize the effects of vibration stimulation of a human subject. Selection of treatment area may be based on theoretical modelling or on results from a previous round of treatment of the particular human subject. The term "treatment area" as used herein refers to the area within a nasal cavity to which vibrations are to be imparted.

The preparative method may further comprise arranging the first and second stimulation members to abut against tissue of the selected treatment area at a first and second pressure of between approximately 20 mbar and 120 mbar. The first and second pressure may be the same or different. Furthermore, the first and the optional second frequency may be selected from a range of between approximately 40 Hz and 100 Hz, such as between approximately 50 Hz and 80 Hz. The first and the optional second frequency may be the same or different.

In another method aspect, there is provided a method of vibration treatment in at least one nasal cavity of a human subject comprising the steps of:

a) inserting a first stimulation member in a first nasal cavity;

b) inserting a second stimulation member in a second nasal cavity;

c) securing said first and second stimulation members such that the stimulation members are in fixed positions within the nasal cavities prior to vibration stimulation;

d) arranging each of said first and second stimulation members to abut against tissue within each of the first and second nasal cavities at a first and second pressure; and e) imparting vibrations to tissue in at least one of said first and second nasal cavities via at least one of said first and second stimulation members.

Vibration treatment in at least one nasal cavity may affect different bodily functions, such as for example the activity of a biological target, such as the hypothalamus and/or the sphenopalatine ganglion. In addition and as described above, several diseases are associated with a dysfunction in the hypothalamus and/or in the sphenopalatine ganglion. By providing vibration treatment according to the present invention to human subjects suffering from diseases related to dysfunctions of hypothalamus and/or sphenopalatine ganglion, the method may thus constitute an alternative treatment form for these diseases.

In one embodiment, the first and second stimulation members are comprised in a device according to the device aspect of the present invention.

In one embodiment, a frequency of the vibrations imparted to the at least one nasal cavity is selected from a range of between 40 Hz and 100 Hz. In one embodiment, said step e) further comprises the step of imparting vibrations at a first frequency to said first nasal cavity and at a second frequency to said second nasal cavity. The first and second frequency can be selected from the range of between approximately 40 Hz and 100 Hz. The first and second frequency may be the same or different. If the first and the second frequencies are different, the difference may lie in the range of 5-30 Hz. Furthermore, the frequencies can be selected in a controlled manner to obtain a desired difference between the frequencies. Further examples of the first and second frequencies are as disclosed in connection with the device aspect of the present invention. The vibrations are, in another embodiment, imparted to one of said first and second nasal cavity at a time. Thus, the vibrations may be imparted sequentially to the nasal cavities.

In one embodiment, an amplitude of the vibrations imparted to the at least one nasal cavity is selected from the range of between approximately 0.05 mm and 20 mm.

In one embodiment, each of the first and second stimulation members is arranged to abut against the tissue of each of the first and second nasal cavities at at least one pressure selected from a range of between approximately 20 mbar and 120 mbar. The pressure exerted on the tissue inside the nasal cavities can be in the range of between approximately 20 mbar and 120 mbar. The pressure exerted on the tissue within the first and second nasal cavities may be the same or different. Further examples of the pressure exerted on the tissue inside the first and second nasal cavities are as disclosed in connection with the device aspect of the present invention.

In one example, the pressure exerted by the first stimulation member against the tissue of the first nasal cavity is in the range of between approximately 80 mbar and approximately 120 mbar and the pressure exerted by the second stimulation member against the tissue of the second nasal cavity is in the range of between approximately 20 mbar and approximately 80 mbar, such as between approximately 20 mbar and approximately 50 mbar. By using two stimulation members at different pressures, different treatment areas may be affected.

The activity in a biological target, such as the hypothalamus, can be measured by different qualitative and/or quantitative methods. In particular, changes in physiological parameters such as for example blood flow, oxygen consumption and metabolic activity are correlated to changes in the level of activity of the biological target, such as the hypothalamus. Depending on the present health condition of a human subject treated with a device according to the first aspect, stimulation may alter the level of activity in the biological target, such as the hypothalamus, somewhat differently. If for example a human subject suffering from a medical condition associated with an abnormal activity in the hypothalamus is treated with a method according to this aspect, vibration stimulation may result in normalized hypothalamic activity. Normalization in this context may refer to a condition where the activity of a biological target is comparable to the activity in surrounding tissue. Thus, a normalized hypothalamic activity may refer to an activity which is comparable to the activity in surrounding brain tissue. The different measures of the activity of the biological target, such as the hypothalamus, can be monitored directly or indirectly.

Furthermore, the same reasoning is valid for other biological targets, such as the sphenopalatine ganglion. The activity in the sphenopalatine ganglion can be measured by different direct or indirect qualitative and/or quantitative methods.

In one embodiment, the method of vibration treatment further comprises the step of) measuring a bodily response to said vibration treatment.

The bodily response is, in one embodiment, a pressure exerted by the tissue on one of said first and second stimulation members in one of the first and second nasal cavities. The first and/or the second stimulation member may comprise a pressure sensor for measuring said pressure exerted on the tissue in the nasal cavity as well as changes in said pressure due to nasal tissue response.

The measure of a bodily response is, in another embodiment, selected from the group consisting of: oxygen consumption as measured by functional Magnetic Resonance Imaging (fMRI), metabolic activity as measured by Positron Emission Tomography (PET), magnetic signals as measured by magnetoencephalography (MEG), electrical signals as measured with electroencephalography (EEG), electrocardiogram (ECG), pain sensation, heart rate, pupil size, body temperature, photoplethysmogram, and blood pressure. Pain sensation can be estimated by the human subject himself/ herself by reference to a visual analogue scale (VAS). In one embodiment, the method further comprises the step of storing data time samples comprising the measured bodily response and at least one associated vibration stimulation parameter. The vibration stimulation parameters are defined above in connection with the system aspect.

In one embodiment, the method further comprises the steps of comparing a previously obtained measure of the bodily response with a later measure of the bodily response; and adjusting at least one of a vibration stimulation parameter and a stimulation cavity if the difference between the later obtained measure and the previously obtained measure lies within a threshold tolerance. This threshold tolerance can be defined as the smallest required change in the input signal for a certain stimulation setting. As can be understood, dependent on a particular desired effect on the measure, the threshold tolerance can be defined somewhat differently.

If the difference between the previous and later obtained values is too small, i.e. lies within the threshold tolerance, or has the wrong sign, a vibrations stimulation parameter or the stimulation cavity may be changed. In one embodiment, said at least one vibration stimulation parameter can be selected from the group consisting of: a frequency, an amplitude, a pressure at which one stimulation member abuts against the tissue inside one nasal cavity, and vibration stimulation duration.

In one embodiment, the method further comprises the steps of comparing a previously obtained measure of the bodily response with a later measure of the bodily response; and adjusting at least one of a vibration stimulation parameter and a stimulation cavity if a desired value of the measure is not approached.

Adjustments of the abovementioned parameters can for example be made randomly until the difference in the input signal is as desired, or systematically by applying settings from a pre-defined grid or by applying a heuristic search. Alternatively, previous parameter settings can be stored together with corresponding obtained values and a direction in a multidimensional parameter space along which the bodily response measure changes the most can be identified. Subsequently, new parameter settings along the identified direction may be tested. Adjusting the above mentioned parameters in such a structured manner may simplify and optimize attainment of a desired level of the bodily response measure.

In one embodiment, the step of adjusting comprises one of: a randomly selected adjustment; an adjustment calculated form a pre-programmed look up table comprising correlations between desired changes in the measure and at least one vibration stimulation parameter; and an adjustment calculated based on correlations between desired changes in the measure and at least one vibration stimulation parameter as derived from previously stored data time samples.

In one embodiment, the desired value of the measure of the bodily response is proportional to a measure of the bodily response previously obtained during the vibration stimulation, or is set to a fraction of an initial measured value or to a pre-programmed desired value.

In one example, pain sensation can be used as a measure of a bodily response to vibration stimulation. This can be useful for example when the patient to be treated with the method is a human subject suffering from cluster headache. The patient to be treated with vibration stimulation may estimate the pain experienced prior to vibration stimulation. During vibration stimulation the patient repeatedly estimates the pain level, and when the pain level reaches an essentially constant level and is not decreasing any more, the vibration stimulation may be switched from one nasal cavity to the other nasal cavity. Alternatively, the vibration stimulation may be terminated.

In another example, the human subject may before and during vibration stimulation treatment estimate the pain level (according to the VAS scale). If the pain level is not reduced after a period of vibration stimulation, a vibration stimulation parameter as defined above may be changed. For example, the frequency can be changed from a relatively higher frequency, such as approximately 70 Hz, to a relatively lower frequency, such as approximately 60 Hz. If the change of frequency is not reducing the pain, another vibration stimulation parameter, such as the pressure at which one of or both of the stimulating member(s) abut(s) against the tissue in nasal cavities may be changed.

The vibration stimulation may be terminated when a threshold value or requirement is reached. The threshold value can be predetermined or calculated, in absolute or relative terms. For example, the threshold value of a measure of bodily response may be defined relatively or absolutely as corresponding to the level of activity of the parts of the tissue surrounding a biological target, e.g. the hypothalamus and/or the sphenopalatine ganglion. The input signal can be compared with a threshold value and the stimulation in one or both nasal cavities can be terminated when the threshold value is reached. Thus, reaching of the threshold value represents the attainment of a desired level of vibration stimulation of the desired biological target, e.g. the hypothalamus and/or the sphenopalatine ganglion, and indicates that the vibration stimulation should either be terminated or the vibration stimulation cavity, when vibrations are imparted sequentially to the nasal cavities, should be switched. Thus, the vibration stimulation in a first nasal cavity may have reached a saturation level where further vibration stimulation in the same nasal cavity may be of no further benefit to the human subject. In such a case, vibration stimulation may be continued in the second nasal cavity of the human subject. Such a threshold value or requirement may be a certain value of a VAS scale, a certain pulse of the human subject, a certain blood pressure, a certain heart rate, or a certain pupil size.

In one embodiment, the method moreover comprises bringing the first and the second stimulation member to essentially non-expanded states and removing the first and the second stimulation member from the first and second nasal cavities.

The human subject subjected to vibration treatment according to the present invention is, in one embodiment, suffering from a disease associated with a dysfunction of the sphenopalatine ganglion. In another embodiment, the human subject is suffering from a disease associated with a dysfunction of the hypothalamus. In yet another embodiment, the human subject is suffering from at least one disease associated with a dysfunction of the hypothalamus and the sphenopalatine ganglion. By using two stimulation members more than one biological target may be affected. Thus, diseases for example associated with a dysfunction of the hypothalamus and/or the sphenopalatine ganglion can be treated such as to reduce, alleviate or in some cases even eliminate the symptoms of the disease.

Examples of diseases that may be treated by the method according to the present invention are, among others, migraine, cluster headache, heart arrhythmia and hypertension.

By providing vibration stimulation to a biological target, such as the hypothalamus and/or the sphenopalatine ganglion, the method may provide an alternative treatment for human subjects suffering from diseases e.g. associated with a dysfunction of the hypothalamus and/or the sphenopalatine ganglion. The method according to the present invention can be used as a complement to or in combination with a conventional treatment of a disease. The method of treatment may be used for treating patients suffering from, for example, migraine, Ménière's disease, hypertension, cluster headache, arrhythmia, ALS, irritable bowel syndrome, sleep disorders, diabetes, obesity, multiple sclerosis, tinnitus, Alzheimer's disease, mood and anxiety disorders and epilepsy.

It should be understood that the embodiments disclosed in relation to a particular aspect of the present invention are, where applicable, relevant also to other aspects of the invention. Further objects and features of the present invention will be apparent from the detailed description and the claims.

BRIEF DESCRIPTION OF THE DRAWINGS

Referring now to the Figures, which are exemplary embodiments, and wherein the like elements are numbered alike:

FIG. 1A is a schematic representation depicting a side view of the human nasal cavity and FIG. 1B is a schematic representation depicting a front view of the human nasal cavities;

FIGS. 3A and 3B are schematic representations depicting one example of a device according to the device aspects of the present invention positioned within the nasal cavities of a human subject;

DETAILED DESCRIPTION OF THE PREFERRED EMBODIMENTS

Embodiments of the present invention will now be described as non-limiting examples and with reference to the Figures.

FIGS. 1A and 1B schematically depict the anatomy of the human nasal cavity. FIG. 1A is a side view schematically depicting a nasal cavity of a human and the position of hypothalamus, A, and sphenopalatine ganglion, B, relative one nasal cavity. FIG. 1B schematically depicts the human nasal cavities seen from the front.

The nose has two cavities, separated from one another by a wall of cartilage called the septum, J, as can be seen in the front view of the nasal cavities in FIG. 1B. The vestibule, C, is the most anterior part of the nasal cavity. On the sides of the nasal cavity are three horizontal outgrowths called nasal conchae or turbinates. The conchae are several thin, scroll-shaped bony elements forming the upper chambers of the nasal cavities. They increase the surface area of these cavities, thus providing for rapid warming and humidification of air as it passes to the lungs. The inferior conchae, D, are the largest of the conchae and are responsible for the majority of the airflow direction, humidification, heating and filtering of air inhaled through the nose. The open region defined by the inferior conchae is called the inferior meatus, G. The middle conchae, E, are smaller. They project downwards over the openings of the maxillary and ethmoid sinuses (not shown), and act as buffers to protect the sinuses from coming in direct contact with pressurized nasal airflow. Most inhaled airflow travels between the inferior conchae and the middle conchae. The open regions defined by the middle conchae, E, are called the middle meatus, H. The superior conchae, F, are smaller structures and serve to protect the olfactory bulb. The superior conchae completely cover and protect the nerve axons piercing through the cribriform plate (a porous bone plate that separates the nose from the brain) into the nose. The open regions defined by the superior conchae, F, are called the superior meatus, I.

Each inferior nasal concha, D, is considered a facial pair of bones since they arise from the maxillae bones and projects horizontally into the nasal cavity. Posterior of the inferior nasal conchae are the middle nasal conchae, E, and superior nasal conchae, F, which arise from the cranial portion of the skull. Hence, these two conchae are considered as a part of the cranial bones.

Figures 2A, 2B:
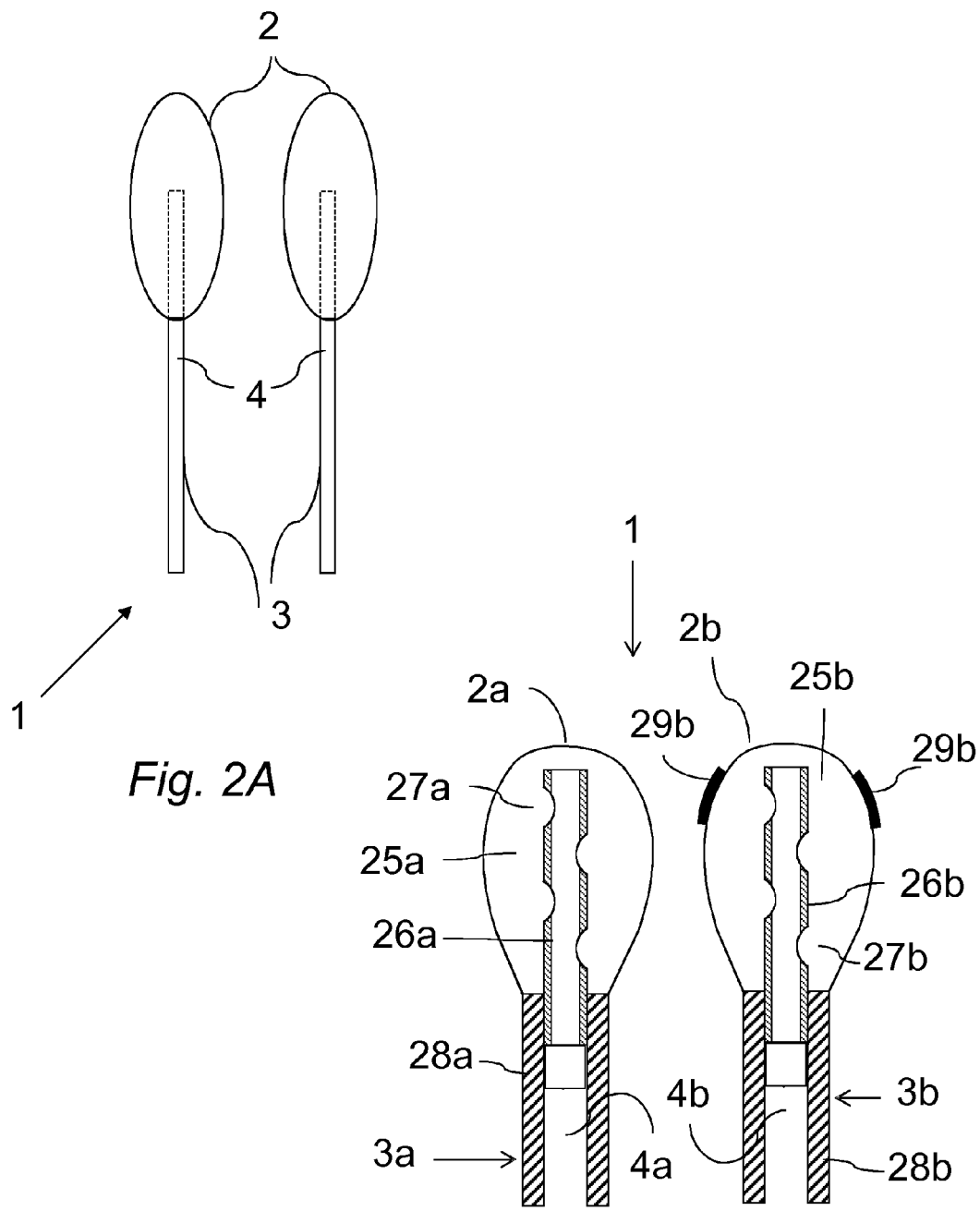
FIGS. 2A and B are schematic representations depicting examples of a device according to the device aspects of the present invention.

With reference to FIG. 2A, a specific example of a device with two stimulation members according to the device aspects of the invention will now be discussed. The device 1 for vibration stimulation in nasal cavities in a human subject comprises a first and a second stimulation member 2 arranged in expanded states and provided with expansion members 3. Each stimulation member 2 is arranged to partly surround one expansion member 3, such that the end portion of the expansion member is located inside the same stimulation member. Alternatively, a stimulation member 2 may be connected adjacent to the end portion of an expansion member 3 (not shown), and consequently arranged to not essentially enclose the expansion member. In another example, a stimulation member 2 may be arranged as a sleeve around an expansion member 3 some distance away from the end portion (not shown). In yet another example, one expansion member is arranged to be connected with two stimulation members (not shown). It is understood that these are only examples of how a device comprising two stimulation members can be arranged and connected to one or two expansion members and that other examples are within the scope of the invention.

The first and second stimulation members may be made of a material such that they do not chemically or biologically affect any body tissue with which they come into contact. For instance, the stimulation members may have no local effect on body tissue. Non-limiting examples of materials are plastic materials or rubber materials. In some instances, the first and/or second stimulation member is made of latex.

The first and/or second stimulation member may furthermore comprise an outer surface that minimizes friction between the first and/or second stimulation member and the surrounding tissue during introduction into and when positioned in the nasal cavities. The first and/or second stimulation member may e.g. be constructed from a material providing a smooth outer surface or be coated with a lubricant, such as e.g. a paraffin solution. Further, the material of the first and/or second stimulation member may be flexible, providing the first and/or second stimulation member with elastic properties.

The size and volume of the first and second stimulation members may consequently vary by an inner pressure. In alternative embodiments, the first and/or second stimulation member is/are made of an inelastic material. In such embodiments, the size of one of or both of the stimulation members is decreased when the first and/or second stimulation member is/are introduced into the nasal cavity. Following introduction into the nasal cavity(s), the first and/or second stimulation member is/are expanded for abutting against tissue surfaces. Furthermore, the first and/or second stimulation member may have partly elastic properties, which makes the first and/or second stimulation member able to both shrink and fold when the first and/or second stimulation member return(s) from an expanded state to an essentially non-expanded state. In such cases, the first and/or second stimulation member may be made of a thin material which can fold. The at least partly non-expanded first and/or second stimulation member can be withdrawn from its position in each nasal cavity.

One non-limiting example of a first and/or second stimulation member is a balloon, which in an at least partly expanded state establishes a contact surface between one stimulation member and the tissue of one nasal cavity. Other examples of a first and/or second stimulation member include bags, bubbles and foam devices.

It is understood that the first and second stimulation members can have the same or different dimension(s), size(s) and volume(s). It is also understood that the first and second stimulation members can be made of the same or different material(s) and have the same or different elastic property(s).

In one example, the expansion member 3 comprises at least one channel 4 for supply of fluid to the stimulation member 2. The stimulation member 2 thus comprises a chamber for containing fluid supplied by the expansion member 3. The chamber walls are defined by the inner surface of the stimulation member 2. The supply of fluid to the stimulation member via the expansion member thus influences the volume and degree of expansion of the stimulation member. To allow free passage of fluid from the expansion member to the stimulation member, the end portion of the expansion member comprises at least one opening. If the end portion of the expansion member 3 is arranged within the stimulation member 2, as for example depicted in FIG. 2A, the end portion may comprise more than one opening for supply of fluid to the stimulation member 2. In another example, one expansion member is arranged to supply fluid to two stimulation members. The parts of the expansion member 3 and stimulation member 2 in contact with the human body typically define a closed system to prevent leakage of fluid to the human body.

The at least one expansion member may for example be freely located at a distance from an inner wall of one stimulation member. Experience has shown that when the device is inserted into the nasal cavity, patients sometimes experience pain, probably due to the comparatively stiff expansion member. When the stimulation member is expanded, the experienced pain sensation subdues. This is likely due to the fact that once expanded, the stimulation member gently push the tissue away from the end of the expansion member. The distance between the end of the expansion member and an inner wall of the stimulation member may be in the range of from 1 to 10 mm, or in the range 4 to 6 mm, or about 5 mm.

Examples of at least one expansion member comprising at least one channel include a pipe, a tubing, a conduit, a cylinder, a tube etc. The at least one expansion member may for instance be made of a plastic, rubber or metal material.

The supply of fluid, e.g. a gas or a liquid, may be controlled by an external apparatus via the at least one expansion member. Such an external apparatus may comprise a cylinder with a movable plunger that, by moving back and forth, can regulate the amount of fluid in the cylinder and thereby regulate the amount of fluid in the at least one expansion member.

In embodiments where a device according to the present invention comprises a first and a second stimulation member and one expansion member, the expansion member is connected to both stimulation members. The device may comprise at least one valve which can control the supply of fluid to both of the stimulation members. In this embodiment, one of or both of the stimulation members can be expanded.

With reference to FIG. 2B, a specific example of a device with two stimulation members and two expansion members according to the device aspects of the invention will now be discussed. The device 1 for vibration stimulation in nasal cavities in a human subject comprises a first stimulation member 2a and a second stimulation member 2b arranged in expanded states and provided with expansion members 3a and 3b. Each stimulation member 2a and 2b is arranged to partly surround the expansion members 3a and 3b, such that the end portion of the expansion member is located inside the respective stimulation member. The interior 25a of the first stimulation member 2a is fluidly connected with the expansion member 3a. The interior 25b of the second stimulation member 2b is fluidly connected with the expansion member 3b. The expansion members 3a and 3b are arranged to expand the stimulation members 2a and 2b. Each of the expansion members 3a and 3b comprises a tubular structure 26a and 26b, which may be arranged at least partly within the stimulation member. The tubular structures 26a and 26b are provided with a plurality of openings 27a and 27b arranged for fluid communication with the interior 25a and 25b of the stimulation members 2a and 2b. Each of the expansion members 3a and 3b moreover comprises an elongated structure 28a and 28b arranged in fluid communication with the interior 25a and 25b of the stimulation members 2a and 2b via the tubular structures 26a and 26b. Each of the elongated structures may be arranged essentially outside the respective stimulation member 2a and 2b, or partly inside the stimulation members 2a and 2b. The elongated structure 28a and 28b may enclose a part of the tubular structure 26a and 26b. Each end portion of the tubular structures 26a and 26b may be provided with an opening for fluid communication with the interior 25a and 25b of the stimulation members 2a and 2b and the elongated structures 28a and 28b. Fluid communication may be accomplished through channels 4a and 4b. The tubular structures 26a and 26b may extend within essentially the entire length of the stimulation members 2a and 2b.

In one embodiment, the tubular structures 26a and 26b leave a distance from an end of the tubular structures 26a and 26b to an inner wall of the stimulation members 2a and 2b, said distance having a length of 5 mm. The circumferential surfaces of the end portions of the tubular structures 26a and 26b are however distanced from the inner walls of the stimulation member.

The tubular structures are sufficiently resilient to allow for insertion and positioning in, sometimes irregular, shape of the nasal cavity. This is particularly important for movements in the sagittal plane since the stimulation members must pass in a vertical bend through the vestibule of the nasal cavity. At the same time, the tubular structures must provide sufficient stiffness in order to avoid accidental bending during introduction into, e.g. the anterior or posterior part of, the nasal cavity. Each of the tubular structures may independently have inner diameter sufficient for avoiding flow resistance, which might cause damping out of vibrations before reaching one of the stimulation members. Furthermore, the tubular structures may have wall thicknesses that, in combination with the plurality of openings, achieve a suitable stiffness. Other material and mechanical properties may also influence the stiffness of the tubular structure.

An end portion of the tubular structures arranged within the stimulation members may be rounded or beveled to prevent the device from getting stuck when introduced into the nasal cavities and to minimize any discomfort for the patient.

The tubular structures comprising the plurality of openings may enable expansion of the stimulation members along their entire length. Since the walls of the nasal cavity varies between individuals and sometimes result in narrow passages, the plurality of openings allows fluid to enter and expand the stimulation members along their entire length. In the embodiment shown in FIG. 2B, the openings have been placed alternating on the two sides of the tubular structures 26a and 26b to ensure that the anisotropic stiffness is sufficient.

At least one of the stimulation members may be provided with a pressure sensor arranged to measure the pressure exerted on the at least one stimulation member by the tissue of the nasal cavity. An example of a pressure sensor 29b is depicted in FIG. 2B.

In embodiments where the device comprises at least one vibration generating member arranged to bring the first and/or the stimulation member to vibrate, the at least one vibration generating member may for example be controlled by an applied electrical voltage supplied from a control unit. In such examples, the at least one vibration generating member may be arranged within the first and/or second stimulation member.

In another example, the vibration generating member is externally arranged. Such an external vibration source, for example a transducer, may be arranged so as to supply vibrations to a fluid contained within the first and/or second stimulation member.

In embodiments where a device according to the present invention comprises two stimulation members and one vibration generating member, the vibration generating member is connected to both stimulation members. In such embodiments, the device may further comprise at least one valve for controlling e.g. the supply of fluid and thus oscillations to each of the two stimulation members. In this embodiment, one stimulation member at a time may impart vibrations. Alternatively, the two stimulation members may impart vibrations at the same frequency.

Vibrations may thus be imparted to the tissue of the at least one nasal cavity via the fluid comprised within the stimulation members. The fluid thus functions as a medium for transferring vibrations via at least one expansion member to the first and/or second stimulation member.

Vibration stimulation of the tissue in the at least one nasal cavity using a device according to the present invention may be conducted at a first and optionally a second frequency of between approximately 40 Hz and 100 Hz. Other frequencies are also anticipated. In embodiments where the device comprises two vibration generating members, the first and second frequency may be the same or different.

In one example, a certain first frequency may be used for stimulating a desired biological target, such as the sphenopalatine ganglion, and a certain second frequency may be used for stimulating the same biological target or optionally a second desired biological target, such as the hypothalamus. In another example, the first and second frequency may be changed during vibration stimulation. In yet another example, one of the stimulation members imparts vibrations at a time. After a period of time, either predetermined or determined during vibration stimulation by the system, an operator, or the human subject himself/herself, the vibrations may be imparted by the other stimulation member positioned in the other nasal cavity.

The first and second stimulation members according to the present invention can be brought to vibrate with various wave patterns depending on field of application. The stimulation members can for instance be brought to vibrate in such a way that the vibrations can be described with a sinus wave or as a square wave.

Interference between vibrations of slightly different frequencies (and with the same amplitude) results in a wave where the amplitude is no longer constant, but change over time. When the two waves are nearly 180 degrees out of phase the maxima of one vibration cancels the minima of the other vibration, whereas when they are nearly in phase their maxima sum up (giving the double amplitude). The result of the vibrations with slightly different frequencies is successive values of maxima and minima that form a wave whose frequency equals the difference between the two starting frequencies. This can be understood mathematically by adding two sine waves with frequencies $f_1$ and $f_2$ respectively.

$$\sin(2\pi f_1 t) + \sin(2\pi f_2 t) = 2\cos\left(2\pi \frac{f_1 - f_2}{2} t\right) \sin\left(2\pi \frac{f_1 + f_2}{2} t\right)$$

If the two starting frequencies are quite close (usually differences of the order of few Hertz), the frequency of the cosine of the right side of the expression above is often too slow to be perceived. Instead, it is perceived as a periodic variation of the sine in the expression whose frequency is the average of the two frequencies. Because the sine part of the right side of the expression above alternates between negative and positive values many times during a period of the cosine part, only the absolute value of the cosine factor is relevant. Therefore, the result is an amplitude modulation with a frequency that is the difference between the two starting frequencies ($f_{mod}=f_1-f_2$).

For example, a first frequency can be 63 Hz and a second frequency can be 73 Hz. This example would give a resulting vibration of 68 Hz (the average of the two frequencies) with amplitude modulated at 10 Hz (the difference between the two frequencies). For example, 68 Hz may be suitable for vibration stimulation of a biological target such as the hypothalamus and 10 Hz may be suitable for vibration stimulation of another biological target, such as the sphenopalatine ganglion.

The first and the second amplitude of the vibrations applied to the tissue of the at least one nasal cavity using a device according to the present invention may be comprised within the range of between approximately 0.05 mm and 20 mm, such as approximately 0.3 mm and 5 mm, but other amplitudes are also anticipated. The first and second amplitude may be the same or different.

The stimulation members may abut against the tissue in the nasal cavities at the same of different pressure(s). The first and second pressure may be within the range of between approximately 20 mbar and 120 mbar, but other pressures are also anticipated.

In one example, a first pressure may be used for vibration stimulation of a first biological target, such as the sphenopalatine ganglion, and a second pressure may be used for vibration stimulation of the same biological target or a second desired biological target, such as the hypothalamus. For example, the first pressure may be in the relatively lower pressure region such as for example 20-50 mbar and the second pressure may be in the relatively higher pressure region such as for example 70-120 mbar.

It should be understood that the first and second frequency, the first and second amplitude and/or the first and second pressure at which the stimulation members abut against the tissue in the nasal cavities which are required for a certain level of vibration stimulation of a biological target, such as the hypothalamus and/or sphenopalatine ganglion, are governed by the nature of the nasal cavities and the sensitivity of the human subject in question. The choice of the first and second frequency, the first and second amplitude and/or the first and second pressure is also governed by what type of treatment is intended to be carried out, i.e. what biological target and what disease should be treated.

In FIGS. 3A and 3B, two stimulation members 2 of a device 1 is at least partly expanded when positioned within the nasal cavities. FIG. 3B shows the position of the two stimulation members within the two nasal cavities. The expansion member 3 is partly located within the stimulation member 2 and partly located outside of the nasal cavity during vibration stimulation (FIG. 3A). The expansion member 3 accordingly provides expansion of the stimulation member 2 to a size and/or volume which is suitable for vibration stimulation. Such expansion may be achieved by supply of fluid to the stimulation member through one or more channels, which are comprised in the expansion member. Vibration stimulation of the tissue in one or two nasal cavity(s) is initiated when the stimulation members have obtained desired volumes. In some cases, where applicable, a higher pressure is used when initiating the vibration stimulation as compared to the pressure exerted on the nasal cavity for the remaining period of vibration stimulation. In such cases, one of or both of the stimulation members may be brought to vibrate when they are at least partly expanded. The stimulation members may when they are at least partly expanded have a circular, oval or droplet shape, depending on the nasal anatomy of the human subject in question.

When the desired effect on a desired biological target, such as hypothalamus and/or sphenopalatine ganglion, is achieved, the vibration stimulation is suitably terminated. The at least partly expanded stimulation members are suitably returned to essentially non-expanded states before being removed from the nasal cavities. Contraction of the stimulation members may for instance be achieved by reduction of fluid pressure within the stimulation members by removal of fluid through the at least one expansion member. When the stimulation members are adequately contracted to be at least partly non-expanded, the stimulation members may be removed from the respective nasal cavity by the human subject himself/herself or by assisting personnel, such as a doctor.

The dimensions of the stimulation member may evidently be adapted to the size and shape of the at least one nasal cavity of the human subject to be treated. The length of one stimulation member when located within one nasal cavity may vary between approximately 3 mm to approximately 100 mm, for example from approximately 40 mm to approximately 60 mm for a Caucasian adult. When the human subject on the other hand is a newborn baby, the length of one stimulation member when located within one nasal cavity may be from approximately 3 mm to approximately 20 mm. It should be understood that the actual length of one stimulation member when positioned within one nasal cavity is dependent on the degree of expansion of the stimulation member and the size of the nasal cavity.

The lateral width of one stimulation member when positioned in one nasal cavity may for instance vary from approximately 1 mm to approximately 40 mm, such as from approximately 10 mm to approximately 20 mm for an adult, depending on the degree of expansion of the stimulation member and the size of the nasal cavity. When positioned in one nasal cavity of a newborn, the stimulation member may be from approximately 1 mm to approximately 3 mm wide. It is understood that, depending on the human subject to be treated, the dimensions of the first and/or second stimulation member may vary outside of the ranges given above.

To render possible a smooth and painless introduction into one nasal cavity, the width of one stimulation member may, when being introduced into the nasal cavity, not exceed the width of the opening of the nasal cavity of the human subject to be treated. In newborns, for instance, one stimulation member may, when being introduced into one nasal cavity, be approximately 1 mm wide. To further facilitate the introduction of one stimulation member into one nasal cavity the stimulation member may be pre-formed with a slight bend to better fit the nasal anatomy.

The device according to the present invention may conveniently comprise a safety valve, which, in case the pressure within the first and/or second stimulation member exceeds a certain maximum value, can release some of the pressure, for example by releasing fluid from the first and/or second stimulation member.

To facilitate insertion and positioning within at least one nasal cavity, the device may be provided with a scale to aid the person performing the vibration stimulation. The at least one expansion member may for example be provided with such a scale, which, together with any prior knowledge of the particular human subject's anatomy, may indicate how far into the nasal cavity a stimulation member has been inserted. Alternatively, the device may be provided with a stop bigger than the opening of the nasal cavity to prevent the stimulation members from being inserted too far into the nasal cavities.

Figure 4:
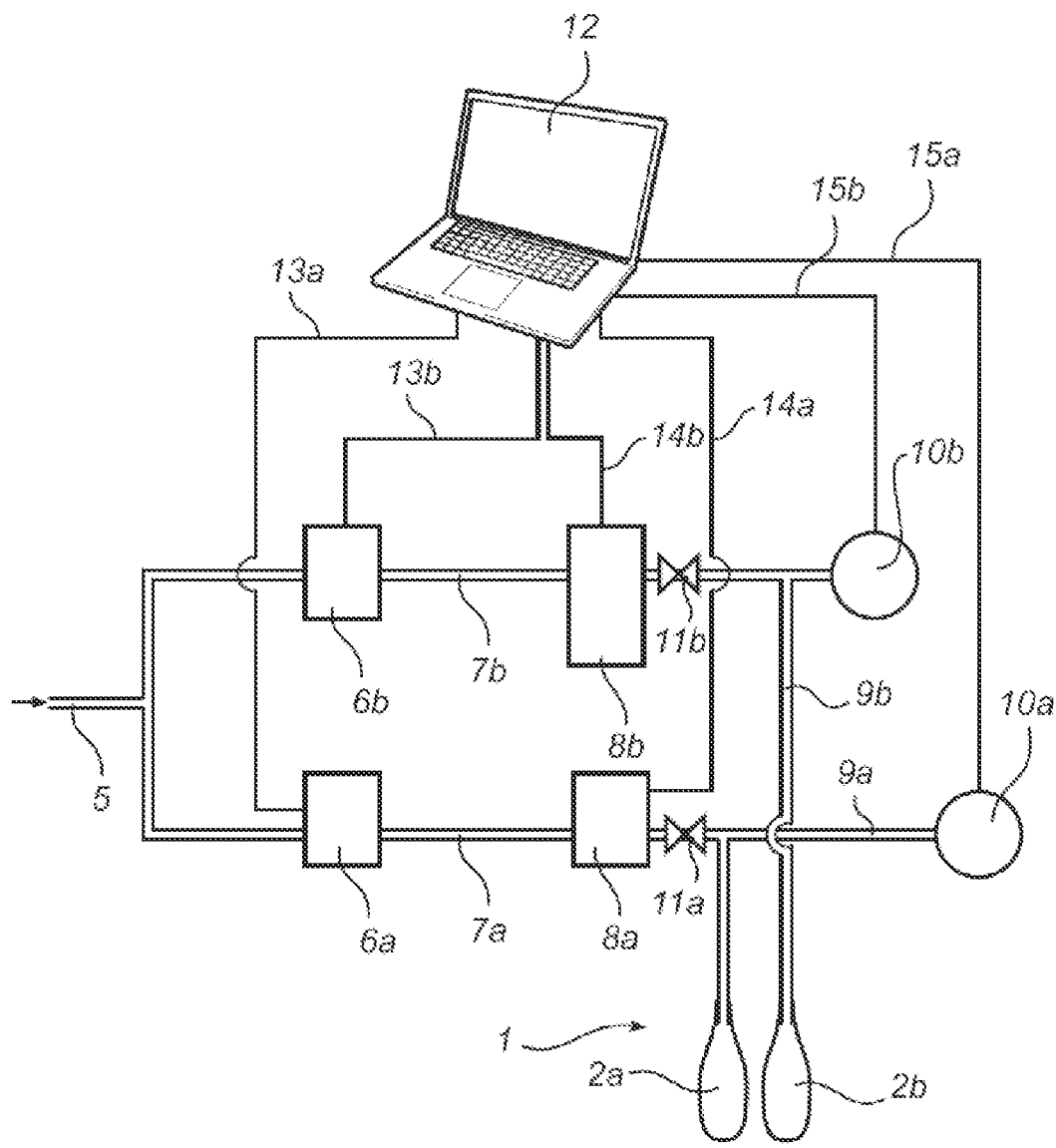
FIG. 4 is a schematic view depicting an example of a system according to the system aspects of the present invention.

With reference to FIG. 4, a specific example of a system according to the system aspect of the invention will now be discussed. The system comprises device 1, having two stimulation members 2 and at least one expansion member 3, as described above. Fluid such as air enters the system via inlet 5. In the pressure regulating modules 6a and 6b, e.g. pressure pumps, the fluid is pressurized before being supplied to at least one of the frequency and amplitude regulating modules 8a or 8b via at least one of tubing 7a or 7b. The frequency and amplitude regulating modules, e.g. oscillation pumps, provide vibrations having a desired frequency and amplitude to the pressurized fluid, which via tubing 9a or 9b and at least one expansion member 3, is supplied to the device 1. The system pressure is monitored by pressure sensors 10a and 10b, e.g. manometers. The system may further comprise safety valves, 11a and 11b, for being able to release fluid, such as gas or liquid, from the system if the system pressure exceeds a maximum level.

In one example, one unit can comprise both of the pressure regulating modules 6a and 6b. In another example, the pressure regulating module 6a is the same as the pressure regulating module 6b. Thus, one pressure regulating module may pressurize the fluid supplied to one of or both of the frequency and amplitude regulating modules 8a and 8b via one or two tubings. In some examples, one unit can comprise both of the frequency and amplitude regulating modules 8a and 8b. In other examples, the frequency and amplitude regulating modules 8a and 8b are the same. One frequency and amplitude regulating modules can provide vibrations via one or two tubings to a device 1. In the same way, one unit may comprise both of the pressure sensors 10a and 10b. In other examples, the pressure sensor 10a is the same as 10b and hence, one pressure sensor can monitor the system pressure. Additionally, the safety valves 11a and 11b can either be positioned within the same unit or be the same valve.

The control unit 12 receives input via lines 13a and 13b from the pressure regulating modules 6a and 6b, via lines 14a and 14b from the frequency and amplitude regulating modules 8a and 8b and via lines 15a and 15b from the pressure sensors 10a and 10b. The control unit further controls the pressure regulating modules 6a and 6b via lines 13a and 13b, and the frequency and amplitude regulating modules 8a and 8b via lines 14a and 14b.

The control unit 12 may moreover comprise a data collection module arranged to collect input from the above mentioned regulating module(s) and sensor(s). The data collection module may moreover obtain an input signal reflecting a measure of a bodily response such as the activity of a biological target e.g. the hypothalamus and/or the sphenopalatine ganglion. Thus, the control unit 12 may receive an input signal from a monitoring device (not shown), such as a functional neuroimaging device. One example of a control unit is a microprocessor comprising suitable peripheral I/O capability executing software e.g. for analyzing the input signal and to determine how to adjust e.g. any of the frequency, the amplitude and the pressure. It is contemplated that other types of a control unit may be used, such as e.g. a personal computer.

An analyzing module (not shown) may moreover be comprised within the control unit. Such an analyzing module provides analysis of the data collected from the separate parts of the system, where applicable, from the device(s), module(s) and/or sensor(s) of the system.

In other examples of a system, a data processing module (not shown) is comprised within the control unit. The data processing module provides calculations of the data collected when running the system. Based on analysis of raw data or calculated data, such as the derivative of the input signal reflecting the measure of a bodily response, the analyzing module is arranged to instruct any one of the regulating modules that may be present in the system, to adjust e.g. the frequency(s), the amplitude(s) and/or the pressure(s). When a measure of a bodily response has reached a saturation level, e.g. as represented by the derivative of the input signal being close to zero, the analyzing module may be arranged to instruct any one of the frequency regulating module(s), the amplitude regulating module(s) and the pressure regulating module(s) to adjust the frequency(s) and/or the amplitude(s) to zero and/or the pressure(s) to reflect atmospheric pressure. When the vibration stimulation has terminated, the stimulation members can return to be at least partly non-expanded whereby the fluid, e.g. gas or liquid, is withdrawn from the at least one expansion member. The at least partly non-expanded stimulation members can then be withdrawn from the nasal cavities of a human subject.

In the system aspects of the present invention, where the system comprises a plurality of geometrically different stimulation members, such stimulation members may be comprised in a kit of different stimulation members. The stimulation members may individually differ in the length and lateral width, for example within the ranges as disclosed above. A plurality of stimulation members may for example comprise two, three, four, five, or more stimulation members having different dimensions and shape. The stimulation members may exhibit different laterally curved and bent forms to facilitate insertion and positioning.

Figure 5:
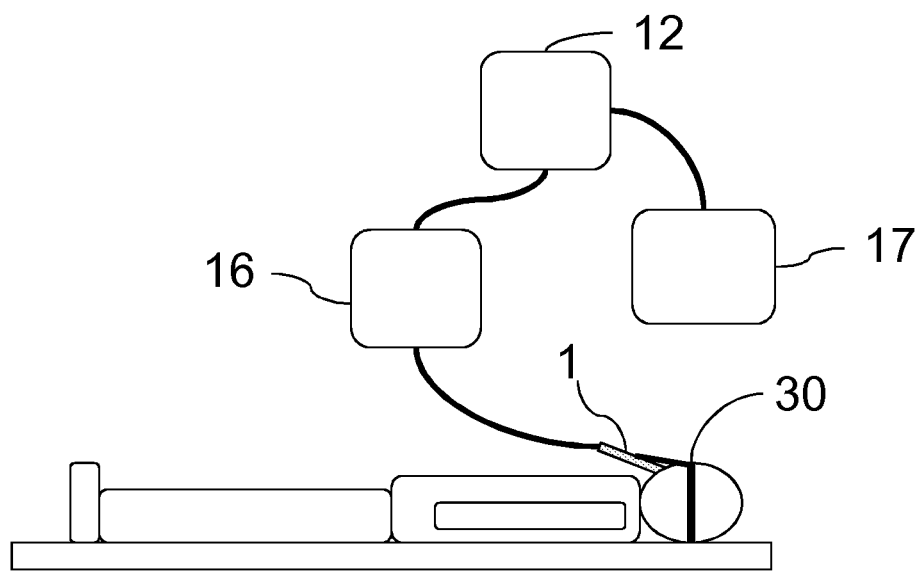
FIG. 5 is a schematic view depicting an example of use of a system according to the system aspects of the present invention.

With reference to FIG. 5, a specific example of use of a system according to the invention will now be discussed. A human subject is subjected to vibration stimulation with a system according to the invention. A device 1 comprising two stimulation members are positioned within each of the nasal cavities of the human subject. The two stimulation members are expanded such that they abut against the tissue of the nasal cavities. An anchoring member 30 is arranged around the patient's head to secure the first and second stimulation members in fixed positions in the first and second nasal cavities during vibration stimulation in at least one nasal cavity. A regulating module 16 for regulating pressure, frequency and amplitude is connected to the device 1 via tubing. The regulating module 16 may comprise at least one of the frequency and amplitude regulating modules 8a and 8b and the pressure regulating modules 6a and 6b. When imparting vibrations to the tissue of the at least one nasal cavity, a bodily response, for example the activity in a biological target, such as in the hypothalamus and/or in the sphenopalatine ganglion, is monitored by monitoring device 17, such as an fMRI instrument. A control unit 12 receives an input signal reflecting a bodily response via line(s) from the monitoring device 17. The control unit comprises a data collection module (not shown) for obtaining the signal. An analyzing module (not shown) and a data processing module (not shown) may moreover be provided within the control unit. The control unit 12 may output instructions for controlling the regulating module 16. Such instructions are based on analysis of the input signal obtained from the monitoring device 17 and aims at adjusting any one of the vibration stimulation parameters of pressure, frequency, or amplitude. In certain instances, when the input signal reflecting a measure of a bodily response reaches a threshold value, the control unit may instruct the regulating module 16 to terminate the vibration stimulation or switch vibration stimulation cavity by first vibrating one stimulation member and then the other stimulation member.

Figure 6:
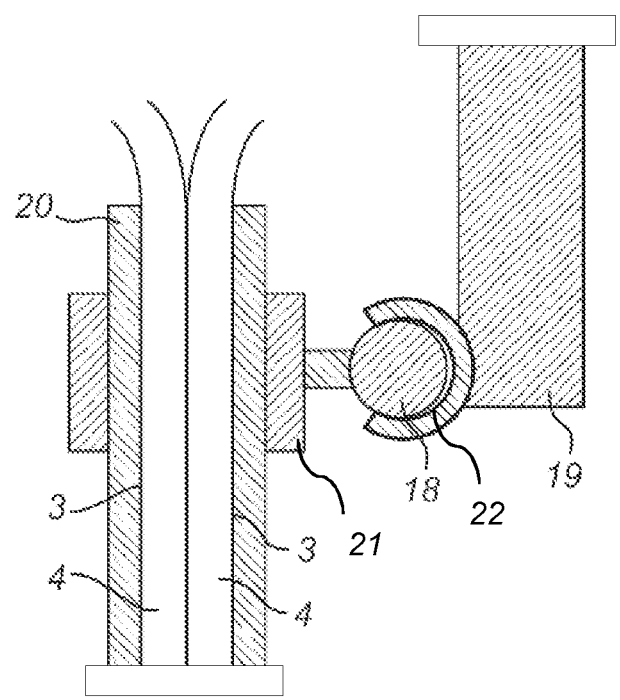
FIG. 6 is a schematic representation depicting one example of an anchoring member and an adjustment member according to the device aspects of the present invention.

With reference to FIG. 6, a specific example of a device according to the present invention will now be discussed. Two stimulation members are provided (not shown) with one expansion member 3 each. The expansion members comprise one channel 4 each. The two expansion members are provided within an outer tubing 20, running from a vibration generating device (not shown) to within a few centimeters of the nose. Attached to the outer tubing 20 is a cuff 21 comprising a ball 18. The ball 18 fits snuggly into a corresponding interface 22 provided on a support arm 19. The fit between the ball and the corresponding interface provide for angle adjustment. The support arm 19 is connected to an anchoring member in the form of a headband or a pair of glasses (not shown). The stimulation members may be inserted into the nasal cavities before the ball is clicked into the corresponding interface. An alternative would be to exclude the outer tubing and instead have two cuffs attached directly to respective expansion member. These would then be attached to one support arm each, these could e.g. be located one on each side of the head.

Preferably, the at least one anchoring member holds the first and the second stimulation member apart when they are introduced into the nasal cavities and when they are positioned into the nasal cavities. Preferably, during vibration stimulation the stimulation members are held separately.

The at least one anchoring member may be provided in the form of e.g. a helmet, a facial mask, a headband or a pair of glasses. Such anchoring member keeps the stimulation members in constant position relative to the nasal cavities even if the human subject moves his/her head during the vibration stimulation or if some other disturbance occurs. The at least one anchoring member also helps to keep the stimulation members in fixed positions relative to each other during the vibration stimulation.

A device with at least one anchoring member preferably comprises at least one adjustment member. With the at least one adjustment member individual variations between human subjects can be adjusted for. The at least one adjustment member may be provided in the form of e.g. a snap wheel, a strap, which is preferably elastic, and a locking member. When for example a snap wheel is used, the angle between one stimulation member and at least one anchoring member can be adjusted in discrete steps. In another example, a cuff with an integrated ball can be used. On the end of one stimulation member a mating part can snap on to the ball positioned at the at least one anchoring member. Preferably, the stimulation members can be introduced into the nasal cavities and thereafter the mating part is snapped onto the ball positioned at the at least one anchoring member.

In some examples, the device may comprise two adjustment members, one for adjusting the position of the first stimulation member and a second for adjusting the position of the second stimulation member. The two adjustment members can be attached to at least one anchoring member, for example a headband with two vertical parts for holding one adjustment member each.

An anchoring member in the form of a headband can hold the stimulation members in fixed positions in the nasal cavities. The headband is preferably elastic to fit closely to the human subject's head. An example of a headband 30 is shown in FIG. 5. In another example, the headband is at least partly non-elastic and the headband can be adjusted around the human subject's head using an adjustment member, such as for example a snap wheel or a screw.

Onto the headband one or two vertical parts can be attached. Each of the vertical parts is possible to adjust both in length and in angle towards the mouth and nose of the human subject. The stimulation members are attached to one of or both of the vertical parts. The stimulation members can be introduced into the nasal cavities prior to attaching the stimulation members to the one or two vertical parts which in turn are attached to the headband.

In one example, one adjustment member can be used to adjust the position of the anchoring member, for example in the form of a headband, around the head of a human subject. Another adjustment member can be used to adjust the length of a vertical part between the anchoring member, for example in the form of a headband, and the nose of a human subject to be treated. Yet another adjustment member can be used to adjust the position of the stimulation members to be inserted into the nasal cavities. The position of the stimulation members inserted into the nasal cavities of a human subject can preferably be adjusted prior to positioning the at least one anchoring member, for example in the form of a headband, onto the head of the human subject to be treated.

In another example, an anchoring member can be in the form of a facial mask. The facial mask is preferably elastic to allow adaptation to variations in head size of human subjects. In one example, the facial mask has holes for the nose and the mouth. In another example, the mask is preferably permeable to air to allow breathing during vibration stimulation. The mask may be fixed onto the face using two straps, preferably elastic straps. Furthermore, the mask may comprise at least one locking member, for holding the stimulation members in fixed positions during vibration stimulation.

A device according to the present invention may further comprise a pair of glasses. The pupil size can be measured using the pair of glasses. For example, a scale can be inserted on the surface of the pair of glasses to simplify measuring of the pupil size prior to and/or during vibration stimulation. The size of the pupil can be used as a measure of a bodily response in order to determine whether the vibration stimulation should be terminated or if the vibration stimulation cavity should be switched. The pair of glasses can preferably be dark, or at least only partly transmit light, for avoiding light coming into the eyes of the human subject during vibration stimulation. This is for example advantageous when treating human subjects suffering from for example severe headache such as migraine.

In one example, the at least one anchoring member may comprise EEG electrodes. The EEG electrodes can be used to measure the brain activity prior to and/or during stimulation. The brain activity can be used as a measure of a bodily response in order to determine whether at least one vibration stimulation parameter should be adjusted, the vibration stimulation should be terminated or if the vibration stimulation cavity (i.e. the first or the second nasal cavity) should be switched.

In another example, the at least one anchoring member may comprise a photoplethysmography sensor which can be attached to an ear lobe of the human subject to be treated. The photoplethysmography sensor may be used to measure the oxygen saturation of the blood. Similarly, the oxygen saturation can be used as a measure of a bodily response in order to determine whether at least one vibration stimulation parameter should be adjusted, the vibration stimulation should be terminated or if the vibration stimulation cavity (i.e. the first or the second nasal cavity) should be switched.

In yet another example, the system according to the present invention may comprise ECG electrodes. The ECG electrodes can be attached onto the chest of the human subject and can be used to measure the heart activity or the pulse of the human subject prior to and/or during vibration stimulation. The ECG electrodes can be connected to a monitoring device in order to record and/or visualize the measurements. The heart activity and/or pulse can similarly be used as a measure of a bodily response in order to determine whether at least one vibration stimulation parameter should be adjusted, the vibration stimulation should be terminated or if the vibration stimulation cavity should be switched.

Figure 7:
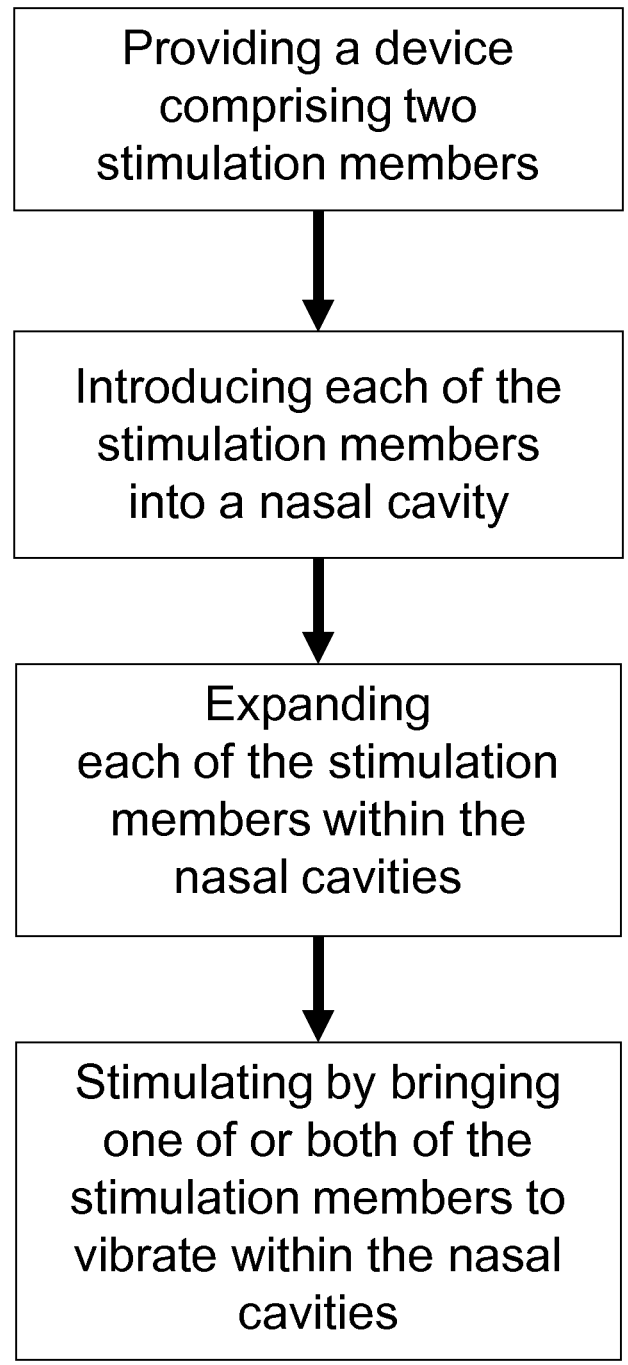
FIG. 7 is a flow chart indicating the steps comprised in one embodiment of a method of vibration treatment according to the present invention.

A method for vibration stimulation in at least one nasal cavity is exemplified below with reference to FIG. 7. A device comprising two stimulation members is provided. Each stimulation member is introduced into a nasal cavity of a human subject. A stimulation member is thus essentially non-expanded when being introduced in order to facilitate passage through the opening of the nasal cavity and to minimize the risk of frightening the human subject by presenting a bulky instrument. When positioned adequately within the nasal cavity, the stimulation member can be expanded such that the stimulation member is brought into close contact with the tissue of the nasal cavity as exemplified in FIGS. 3A and 3B. It is to be understood that the volume of the stimulation member(s) may be adjusted to the size of the nasal cavity(s) such that good contact is achieved with the tissue prior to vibration stimulation. A good and/or close contact refers to such a contact that the available outer surface of a stimulation member when it is at least partly expanded essentially abuts against the surface of the tissue.

Subsequently, one of or both of the stimulation member(s) is/are brought to vibrate to stimulate a biological target, such as for example hypothalamus and/or sphenopalatine ganglion, either simultaneously or sequentially.

For example, a device according to the first aspect of the present invention may be used for simultaneous vibration stimulation in the nasal cavities or for sequential vibration stimulation in one nasal cavity at a time. It should be understood that pressure(s) and frequency(s) may be the same or different for sequential and/or simultaneous vibration stimulation in the nasal cavities. Two different frequencies with a phase and/or amplitude difference may be applied during simultaneous vibration stimulation to achieve an interference effect.

Prior to vibration stimulation, the method may involve selecting from a plurality of stimulation members having individually different geometry, two stimulation members having a geometry suitable for the two nasal cavities of the human subject to be treated. As previously discussed, certain human subjects might require different stimulation members having a certain shape, length and width/diameter.

In addition, vibration stimulation duration suitable for the human subject in question may be selected prior to initiating the vibration stimulation in at least one nasal cavity. Such selection may comprise selecting a minimum duration for standard vibration stimulation, such as at least 5 minutes in total. Alternatively, the vibration stimulation duration may be defined as the period of treatment at which the measure of a bodily response has fulfilled a predetermined requirement, such as returning to a normal pulse and/or a normal pupil size. In the context of the present invention, normal refers to a state of a human subject being healthy and is preferably not experiencing pain, such as headache e.g in the form of migraine and cluster headache, and is preferably not experiencing irregular heartbeats. In another example, the predetermined requirement is that the human subject being treated is experiencing pain corresponding to a certain value of the VAS scale. Other treatment regimes involves selecting a duration of treatment in a first and then in a second nasal cavity.

As described in connection with the system and the method aspects of the present invention, the vibration stimulation of a desired biological target may be terminated when a desired level of vibration stimulation has been reached.

When the method as disclosed herein involves treatment of a disease associated with hypothalamic dysfunction and/or sphenopalatine ganglion dysfunction, it should be understood that such treatment may suitably be performed preventive or acute.

What is claimed is:
1. A device for vibration stimulation in at least one nasal cavity of a human subject, comprising:
 a first stimulation member arranged to be introducible into a first nasal cavity, to be expanded within the first nasal cavity and to abut against tissue in the first nasal cavity;
 a first expansion member arranged to expand the first stimulation member; the first expansion member comprising a first tubular structure arranged at least partly within the first stimulation member, wherein the first tubular structure is provided with a plurality of openings arranged for fluid communication with the first stimulation member, and wherein the first tubular structure has a bending stiffness in a first direction, perpendicular to a longitudinal direction of the first tubular structure, the bending stiffness in the first direction being different from a bending stiffness in a second direction, perpendicular to said first direction and to the longitudinal direction of the first tubular structure;
 a second stimulation member arranged to be introducible into a second nasal cavity, to be expanded within the second nasal cavity and to abut against tissue in the second nasal cavity; and
 a second expansion member arranged to expand the second stimulation member; the second expansion member comprising a second tubular structure arranged at least partly within the second stimulation member, wherein the second tubular structure is pro- vided with a plurality of openings arranged for fluid communication with the second stimulation member;

wherein at least one of the first and second stimulation members is arranged to impart vibrations to the tissue in at least one of the first and second nasal cavities.

2. The device according to claim 1, wherein each one of the first and second stimulation members is arranged to impart vibrations at at least one frequency selected from a range of between 40 Hz and 100 Hz.

3. The device according to claim 1, wherein the first stimulation member is arranged to impart vibrations at a different frequency than the second stimulation member.

4. The device according to claim 3, wherein the difference between the frequencies imparted by the first stimulation member and the second stimulation member is in the range of 5-30 Hz.

5. The device according to claim 1, wherein each of the first and second stimulation members is arranged to abut against the tissue of each of the first and second nasal cavities at at least one pressure selected from a range of between approximately 20 mbar and 120 mbar.

6. The device according to claim 1, wherein at least one of the first and second stimulation members is arranged to impart vibrations at an amplitude in the range of between approximately 0.05 mm and 20 mm.

7. The device according to claim 1, wherein the anchoring member is selected from the group consisting of: a helmet, a headband, a facial mask and a pair of glasses.

8. A system for vibration stimulation in at least one nasal cavity of a human subject, comprising:
a device according to claim 1; and at least one of:
a frequency regulating module arranged to adjust the frequency(s) of the vibrations imparted by one of or both of the first and second stimulation member(s) of the device to one of or both of the first and second nasal cavities;
an amplitude regulating module arranged to adjust the amplitude(s) of the vibrations imparted by one of or both of the first and second stimulation member(s) of the device to one of or both of the first and second nasal cavities; and
a pressure regulating module arranged to adjust the pressure(s) at which one of or both of the first and second stimulation member(s) of the device abut(s) against the tissue of one of or both of the first and second nasal cavities.

9. The system according to claim 8, further comprising:
a data collection module arranged to obtain and store data time samples comprising an input signal reflecting a measure of a bodily response to the vibration treatment.

10. The system according to claim 9, wherein the data time samples further comprises a pressure at which at least one of the first and second stimulation member(s) abut(s) against the tissue of the respective nasal cavity.

11. The system according to claim 9, wherein the input signal reflecting a measure of a bodily response is selected from the group consisting of: oxygen consumption as measured by fMRI, metabolic activity as measured by PET, magnetic signals as measure by MEG, electrical signals as measured with EEG, electrocardiogram (ECG), pain sensation, heart rate, pupil size, body temperature, photoplethysmogram, and blood pressure.

12. The system according to claim 9, wherein the data time samples comprises at least one associated vibration stimulation parameter and the measured bodily response.

13. The system according to claim 9, wherein the at least one vibration stimulation parameter is selected from the group consisting of:
a frequency of the vibrations imparted by one of or both of the first and second stimulation member(s);
an amplitude of the vibrations imparted by one of or both of the first and second stimulation member(s);
a pressure at which one of or both of the first and second stimulation member(s) abut(s) against the tissue of one of or both of the first and second nasal cavities(s);
a difference between the frequencies of the vibrations imparted by the first and second stimulation members;
a difference between the amplitudes of the vibrations imparted by the first and second stimulation members;
a difference between the pressures at which the first and second stimulation members abut against the tissue of the first and second nasal cavities, and
a vibration stimulation duration.

14. The system according to claim 13, further comprising:
an analyzing module arranged to analyze the stored input signal to determine if a desired value of the measure is approached, wherein, if the desired value is not approached, the analyzing module is arranged to instruct at least one of the frequency regulating module, the amplitude regulating module and the pressure regulating module to adjust said at least one vibration stimulation parameter, by way of one of
a random adjustment;
an adjustment calculated from a pre-programmed look-up table comprising correlations between desired changes in the measure of bodily response and at least one vibration stimulation parameter, and
an adjustment calculated based on correlations between desired changes in the measure of bodily response and at least one vibration stimulation parameter as derived from the previously stored data time samples.

15. The system according to claim 14, wherein a desired value of the measure of the bodily response is proportional to a measure of the bodily response previously obtained during the vibration stimulation, or is set to a fraction of an initial measured value or to a pre-programmed desired value.

* * * * *